(12) United States Patent
Monteiro et al.

(10) Patent No.: US 7,527,949 B2
(45) Date of Patent: May 5, 2009

(54) POLYSACCHARIDES OF *HELICOBACTER PYLORI*

(75) Inventors: Mario Artur Monteiro, Guelph (CA); James Fulginiti, Nanuet, NY (US); Deborah Ann Dilts, West Nyack, NY (US)

(73) Assignee: Wyeth Holdings Corporation, Madison, NJ (US)

( * ) Notice: Subject to any disclaimer, the term of this patent is extended or adjusted under 35 U.S.C. 154(b) by 281 days.

(21) Appl. No.: 10/976,285

(22) Filed: Oct. 28, 2004

(65) Prior Publication Data

US 2005/0118197 A1 Jun. 2, 2005

Related U.S. Application Data

(60) Provisional application No. 60/516,644, filed on Oct. 31, 2003.

(51) Int. Cl.
*C12P 19/04* (2006.01)
(52) U.S. Cl. ............ 435/97; 435/101; 435/200; 536/119; 536/123.1
(58) Field of Classification Search .............. None
See application file for complete search history.

(56) References Cited

U.S. PATENT DOCUMENTS

| | | | |
|---|---|---|---|
| 4,284,537 A | 8/1981 | Beachey | |
| 4,356,170 A | 10/1982 | Jennings et al. | |
| 4,619,828 A | 10/1986 | Gordon | |
| 4,663,160 A | 5/1987 | Tsay et al. | |
| 4,673,574 A | 6/1987 | Anderson | |
| 4,761,283 A | 8/1988 | Anderson | |
| 4,762,713 A | 8/1988 | Anderson | |
| 4,789,735 A | 12/1988 | Frank et al. | |
| 4,902,506 A | 2/1990 | Anderson et al. | |
| 5,032,505 A * | 7/1991 | Pierce et al. | ............ 435/15 |
| 5,097,020 A | 3/1992 | Anderson et al. | |
| 5,360,897 A | 11/1994 | Anderson et al. | |
| 6,007,818 A | 12/1999 | Moreau | |

(Continued)

FOREIGN PATENT DOCUMENTS

EP 0 206 852 A1 5/1986

(Continued)

OTHER PUBLICATIONS

Drouet, Emmanuel et al, Infection and Immunity, vol. 61(6), pp. 2732-2736, Jun. 1993, Partial characterization of an external polysaccharide of *Helicobacter pylori* by using an immunoglobulin M monoclonal antibody.*

(Continued)

*Primary Examiner*—Mark Navarro
*Assistant Examiner*—Ginny Portner
(74) *Attorney, Agent, or Firm*—Kelly M. Sullivan; J. Darrell Fontenot

(57) ABSTRACT

The invention is directed to immunogenic compositions comprising polysaccharides and polysaccharide-protein conjugates that are useful to induce or detect the production of antibodies specific for *H. pylori*. The invention is also directed to methods of purifying the *H. pylori* polysaccharides from bacteria. The polysaccharide may be incorporated into an immunogenic composition or used in vitro to assay for the presence of *H. pylori* antibodies in a sample or biological fluid.

56 Claims, 4 Drawing Sheets

U.S. PATENT DOCUMENTS

| | | | |
|---|---|---|---|
| 6,045,805 | A | 4/2000 | Moreau |
| 6,274,356 | B1* | 8/2001 | Chung et al. ............... 435/101 |
| 6,960,344 | B2* | 11/2005 | Marciani ................ 424/193.1 |
| 7,364,919 | B2* | 4/2008 | Penades et al. ............ 436/524 |
| 2002/0160009 | A1* | 10/2002 | Cutler et al. ............ 424/184.1 |
| 2004/0052729 | A1* | 3/2004 | Penades et al. ........... 424/1.73 |
| 2006/0058506 | A1* | 3/2006 | Bundle et al. .............. 530/350 |
| 2006/0067888 | A1* | 3/2006 | Marchal et al. .............. 424/9.2 |
| 2006/0089330 | A1* | 4/2006 | Seeberger et al. ............. 514/54 |
| 2006/0104975 | A1* | 5/2006 | Geijtenbeek et al. ..... 424/144.1 |
| 2006/0183710 | A1* | 8/2006 | Kuo et al. ..................... 514/54 |
| 2006/0287276 | A1* | 12/2006 | Rhoades et al. .............. 514/54 |
| 2007/0037248 | A1* | 2/2007 | Bobrowicz et al. ......... 435/69.1 |
| 2007/0254344 | A1* | 11/2007 | Matsuo et al. ................ 435/97 |
| 2007/0259379 | A1* | 11/2007 | Marth ........................ 435/7.2 |
| 2007/0286896 | A1* | 12/2007 | Yamazaki et al. ........... 424/450 |
| 2008/0019918 | A1* | 1/2008 | Aoki et al. ................... 424/9.3 |
| 2008/0146522 | A1* | 6/2008 | Coombe et al. ............... 514/56 |
| 2008/0220988 | A1* | 9/2008 | Zhou ........................... 506/18 |
| 2008/0293620 | A1* | 11/2008 | Marchal et al. ................ 514/8 |

FOREIGN PATENT DOCUMENTS

| | | | |
|---|---|---|---|
| EP | 0 245 045 | B1 | 11/1993 |
| EP | 0 899 343 | | 3/1999 |
| EP | 0899343 | * | 3/1999 |
| JP | 05 115292 | | 5/1993 |
| JP | 05115292 | * | 5/1993 |

OTHER PUBLICATIONS

Moens, et al, Arch. Microbiol, 1997, vol. 168, pp. 169-175, Glycoproteins in prokaryotes.*

Kwon, Y.T. et al, Organic Letters, 2004, vol. 6(22) pp. 3901-3904, Synthesis of the trisaccharide repeating unit of the atypical O-antigen polysaccharide from Danish Helicobacter strains employing the 2/carboxybenzyl Glycoside.*

Ajisaka, Katsumi et al, Carbohydrate Research, vol. 270, pp. 123-130, 1995, Enzymatic synthesis of mannobioses and mannotrioses by reverse hydrolysis using alpha mannosidase from *Aspergillus niger*.*

Kouwijzer, M et al, Journal of Molecular Structure, (Theochem), pp. 201-210, vol. 395-396, 1997, Conformational analysis of the trimannose Manalpha(1-2)[Man alpha1-6)]ManB using the CHEAT95 force field evaluation of the additivity principle.*

Han, Yongmoon et al, Infection and Immunity, vol. 68(3), pp. 1649-1654, Mar. 2000, Protection against Candidiasis by an immunoglobulin G3 (IgG3) monoclonal antibody specific for the same mannotriose as an IgM protective antibody.*

Karlsson, Karl-Anders, The Human gastric colonizer *Helicobacter pylori*: a challenge for host-parasite glycobiology, Glycobiology, vol. 10(8), pp. 761-771, 2000.*

Stratton, Charles W. et al, J. of Antimicrobial Chemotherapy, 1999, pp. 659-666, vol. 43.*

Karlsson, Karl-Anders, Glycobiology, vol. 10(8), pp. 761-771, 2000, Mini Review, The human gastric colonizer *Helicobacter pylori*: a challenge for host-parasite glycobiology.*

Molecular Immunology, vol. 22(1) pp. 29-36, 1985, Richter, AW et al, Studies on artificial oligosaccharide-protein antigens: induction of precipitating antibodies to defined epitoeps on natural and synthetic dextrans and mannans.*

Jawahar S. Sawardeker, et al., Analytical Chemistry, vol. 37, No. 12, pp. 1602-1604, 1965.

O. Westphal and K. Jann, Bacterial Lipopolysaccharides, vol. 5, pp. 83-91, 1965.

Emil C. Gotschlich, et al., J. Exp. Med., vol. 129, pp. 1349-1365, 1969.

Barbara A. Schwartz and Gary R. Gray, Archives of Biochemistry and Biophysics, vol. 181, pp. 542-549, 1977.

Karin Leontein, et al., Carbohydrate Research, vol. 62, pp. 359-362, 1978.

Chiayung Chu, et al., Infection and Immunity, vol. 40, No. 1, pp. 245-256, 1983.

Porter Anderson, Infection and Immunity, vol. 39, No. 1, pp. 233-238, 1983.

Ionel Ciucanu and Francisc Kerek, Carbohydrate Research, vol. 131, pp. 209-217, 1984.

Barry J. Marshall and J. Robin Warren, The Lancet, vol. 1, No. 8390, pp. 1311-1314, 1984.

Arthur Morris and Gordon Nicholson, The American Journal of Gastroenterology, vol. 82, No. 3, pp. 192-199, 1987.

Martha Lepow, MD, Pediat. Infect. Dis. J., vol. 6, No. 8, pp. 804-807, 1987.

William E. Dick, Jr. and Michel Beurret, Contributions to Microbiology and Immunology, Conjugate Vaccines, vol. 10, pp. 48-114, 1989.

Julie Parsonnet, M.D., et al., N. Engl. J. Med., vol. 325, No. 16, pp. 1127-1131, 1991.

Agnes Labigne and Hilde De Reuse, Infectious Agents and Disease, vol. 5, pp. 191-202, 1996.

Giuseppe Del Giudice, et al., Annu. Rev. Immunol., vol. 19, pp. 523-563, 2001.

Mario A. Monteiro, Advances in Carbohydratre Chemistry and Biochemistry, vol. 57, pp. 99-158, 2001.

* cited by examiner

POLYSACCHARIDES OF *HELICOBACTER PYLORI*

This application claims priority from copending Provisional Application No. 60/516,644 filed Oct. 31, 2003 the entire disclosure of which is hereby incorporated by reference in its entirety.

FIELD OF THE INVENTION

The invention relates to the field of polysaccharides of *Helicobacter pylori*.

BACKGROUND OF THE INVENTION

The cause of peptic ulcer disease was, for many years, focused on the role of gastric acid in the genesis of peptic ulceration. It was found that suppression of acid production with histamine 2 (H2)—receptor antagonists was effective in healing acute ulcers, but the recurrence rate during the first year could be as high as 90%. Unfortunately, a misconception about the cause produced treatments that may have been effective in healing the ulcers but could not cure the disease.

Eventually, an infectious agent as the cause began to be explored after the isolation of gram-negative spiral-shaped bacteria from biopsy specimens obtained from human subjects with gastritis and peptic ulcers was reported. See Marshall B. J. and Warren J. R., *Unidentified curved bacilli on gastric epithelium in active chronic gastritis*, Lancet (i): 1311-1315 (1984). The infectious agent was initially identified as *Campylobacter pyloridis*. Subsequent studies have confirmed that this bacterium, currently referred to as *Helicobacter pylori* (*H. pylori*), is a major cause of chronic diffuse superficial (type B) gastritis and gastroduodenal ulcer disease. Further evidence to support the role of *H. pylori* comes from studies using human volunteers that were challenged with *H. pylori* in order to fulfill Koch's postulates. See Marshall B. J., et al., *Med. J. Aust.* 142: 436-439 (1985); and Morris A., et al., *Am. J. Gastroenterol.* 82: 192-199 (1987).

*H. pylori* bacteria infect more than 50% of the world's human population. See Mitchell, H. M., *Curr. Top. Microbiol. Immunol.*, 241:11-30 (1999). However, it is not understood why many individuals who have been infected for years do not develop any symptoms of gastritis or ulcer disease while others do. There is also a reported connection between *H. pylori* infection and the development of gastric carcinoma. See Parsonnett J., *N. Engl. J. Med.* 325:1127-1131 (1991) and Nomura A., et al., N. Engl. J. Med.; 325:1132-1136 (1991). It is now fairly clear that *H. pylori* infections are responsible for the onset of chronic superficial gastritis, chronic active gastritis, peptic ulcers and gastric cancer. See Parsonnet et al, *N. Engl. J. Med.*, 330:1267-1271 (1994). Consequently, this gastric bacterium has been classified as a category 1 (definite) human carcinogen. See Labigne, A. et al., *Infect. Agent Dis.*, 5:191-202 (1996).

The leading treatment of *H. pylori* infection in humans is typically carried out by combining one proton pump inhibitor and two antibiotics. See Unge, P. *Curr. Top. Microbiol Immunol.*, 241:261-300 (1999). This combination therapy must be maintained for a week or two, and it can eliminate the infection in 80 to 90% of those treated. See Unge, P. *Curr. Top. Microbiol. Immunol.*, 241:261-300 (1999). Even though antibiotic treatment is effective, there are problems associated with its use. Compliance with the antibiotic treatment regimen is a problem area for antibiotic treatment of *H. pylori* infection because of the large number of pills and the frequency of administration that are required. See Bell, G. D. et al., Ailment Pharmacol. Ther. 6:427-35 (1992). A more troubling treatment issue involves the emergence of strains of *H. pylori* that are resistant to the most commonly prescribed antibiotics. Antibiotic resistance is becoming a frequently reported limitation to successful treatment of *H. pylori* infections. See Graham, D. Y., Gastroenterology 115:1272-77 (1998). Finally, treatment of *H. pylori* with antibiotic therapies is only offered to those infected patients who are currently showing obvious symptoms, thus the vast majority of asymptomatic people are left untreated awaiting the development of chronic gastritis and eventually gastric cancer.

An effective immunogenic composition to prevent infection would overcome many of the problems and limitations associated with antibiotic based treatments of *H. pylori* infection. Numerous immunogenic composition candidates have been explored for use in inducing protection against *H. pylori* infection. Several *H. pylori* antigens, due to their role in the bacterial life cycle, have been investigated as possible subunit immunogens. Numerous *H. pylori* immunogens have been described including urease, vacuolating cytotoxin (VacA), cytotoxin associated gene A (cagA) and neutrophil activating protein (NAP), and yet, to date there is no immunogenic composition available for either preventing infection with *H. pylori* or for therapeutically treating those infected. See Giudice, G. D. et al., *Annu. Rev. Immunol.*, 19:523-563 (2001), the disclosure of which is hereby incorporated by reference in its entirety. A need exists for safe and protective immunogens and immunization strategies for preventing infection with *H. pylori* and for therapeutically treating infected people.

SUMMARY OF THE INVENTION

In a particular embodiment, the invention comprises an isolated bacterial polysaccharide, comprising a repeating trisaccharide unit with a structure of

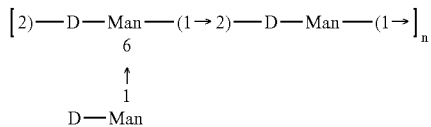

wherein n is an integer of less than 100.

In one embodiment, the invention comprises a polysaccharide, comprising a repeating trisaccharide unit with a structure as shown in FIG. 2, and wherein n is an integer of less than 100.

In a certain embodiment, the invention comprises a branched polymannose polysaccharide, wherein the mannose residues are connected as shown below

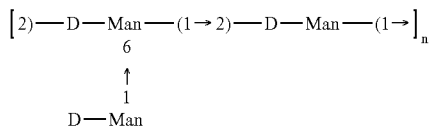

wherein n is an integer of less than 100.

In one embodiment, the present invention comprises an immunogenic composition comprising an immunogenic amount of a polysaccharide and a pharmaceutically acceptable diluent, and wherein said polysaccharide comprises a repeating trisaccharide unit with a structure of $$[2)-D-Man-(1\to2)-D-Man-(1\to]_n$$
$$\begin{array}{c}6\\\uparrow\\1\\D-Man\end{array}$$

wherein n is an integer of less than 100. In another embodiment, the immunogenic composition further comprises an adjuvant.

In another embodiment, the present invention comprises a immunogenic composition comprising an immunogenic amount of a polysaccharide-protein conjugate and a pharmaceutically acceptable diluent, and wherein said polysaccharide comprises a repeating trisaccharide unit with a structure of $$[2)-D-Man-(1\to2)-D-Man-(1\to]_n$$
$$\begin{array}{c}6\\\uparrow\\1\\D-Man\end{array}$$

wherein n is an integer of less than 100 and whereas said polysaccharide and said protein are connected through covalent bonds. In another embodiment, the pharmaceutical formulation further comprises an adjuvant.

In another embodiment, the invention is directed to a polysaccharide-protein conjugate comprising an immunogenic amount of an extracellular polysaccharide covalently linked to a protein, wherein said polysaccharide comprises a repeating trisaccharide unit with a structure of $$[2)-D-Man-(1\to2)-D-Man-(1\to]_n$$
$$\begin{array}{c}6\\\uparrow\\1\\D-Man\end{array}$$

wherein n is an integer of less than 100.

In a particular embodiment, the invention also comprises a method of immunizing a mammal against *H. pylori* infection comprising administering to an individual an immunogenic amount of a polysaccharide comprising a repeating trisaccharide unit with a structure of $$[2)-D-Man-(1\to2)-D-Man-(1\to]_n$$
$$\begin{array}{c}6\\\uparrow\\1\\D-Man\end{array}$$

wherein n is an integer of less than 100.

In one embodiment, the invention comprises a method of immunizing a mammal against *H. pylori* infection comprising administering to an individual an immunogenic amount of a polysaccharide-protein conjugate, wherein said polysaccharide comprises a repeating trisaccharide unit with a structure of $$[2)-D-Man-(1\to2)-D-Man-(1\to]_n$$
$$\begin{array}{c}6\\\uparrow\\1\\D-Man\end{array}$$

wherein n is an integer of less than 100 and wherein said polysaccharide and said protein are connected through covalent bonds.

In a particular embodiment, the invention comprises a method of detecting whether an individual is infected with *H. pylori* comprising:

(i) isolating a polysaccharide from *H. pylori*, wherein said polysaccharide comprises a repeating trisaccharide unit with a structure of $$[2)-D-Man-(1\to2)-D-Man-(1\to]_n$$
$$\begin{array}{c}6\\\uparrow\\1\\D-Man\end{array}$$

wherein n is an integer of less than 100;

(ii) producing a monoclonal antibody that specifically recognizes and binds to said polysaccharide;

(iii) reacting said monoclonal antibody with gastric fluid including saliva of patients potentially infected with *H. pylori*; and (iv) detecting the presence of antibody bound to *H. pylori* polysaccharide.

In another embodiment, the invention comprises a method of detecting whether an individual has been infected with or exposed to *H. pylori* comprising:

(i) isolating a polysaccharide from *H. pylori*, wherein said polysaccharide comprises a repeating trisaccharide unit with a structure of $$[2)-D-Man-(1\to2)-D-Man-(1\to]_n$$
$$\begin{array}{c}6\\\uparrow\\1\\D-Man\end{array}$$

wherein n is an integer of less than 100;

(ii) reacting antibodies obtained from a potentially infected subject with said polysaccharide; and (iii) detecting whether antibodies from a potentially infected subject recognize and bind to said polysaccharide In a certain embodiment, the polysaccharides of the invention are useful in diagnostic and analytical assays for detecting present and past infections of *H. pylori* in a subject.

In another embodiment, the invention comprises a process for isolating a polysaccharide, wherein said polysaccharide comprises a repeating trisaccharide unit with a structure of

wherein n is an integer of less than 100, comprising the steps of: a) extracting *H. pylori* bacteria with a mixture of water and phenol; b) size fractionating the water layer of step a) by column chromatography; and c) selecting those fractions containing said polysaccharide.

In a certain embodiment, the repeating polysaccharide structure is a polysaccharide of *H. pylori*. In one embodiment, the polysaccharide is a capsule polysaccharide from *H. pylori*. In another embodiment, the polysaccharide is isolated from *H. pylori*. In an alternate embodiment, the polysaccharide is purified from *H. pylori*. In still another embodiment, the polysaccharide is isolated and purified from *H. pylori*. Alternatively, in another embodiment of the invention the polysaccharide is chemically synthesized. In yet another embodiment of the invention the polysaccharide is prepared by expression in a surrogate host after cloning and expressing the biosynthetic pathway.

One embodiment of the invention comprises an immunogenic composition comprising a polysaccharide-protein conjugate. In one embodiment of this aspect, the polysaccharide and the protein are conjugated together directly through a covalent bond. In another embodiment of this aspect, the polysaccharide and the protein are conjugated together through a linker.

In a particular embodiment of the present invention, the polysaccharide and the protein are conjugated together to form an immunogenic polysaccharide-protein conjugate or immunoconjugate. In one embodiment, of this aspect of the invention, there are between about 1 and about 50 molecules of conjugated polysaccharide per molecule of protein. Alternatively, in another embodiment, there are between about 1 and about 20 molecules of conjugated polysaccharide per molecule of protein. In a preferred embodiment, there are between about 2 and about 20 molecules of conjugated polysaccharide per molecule of protein.

In a particular embodiment the invention comprises an immunogenic amount of a polysaccharide-protein conjugate. In one embodiment, the protein is any native or recombinant bacterial protein. In another embodiment, the protein is a protein selected from the group consisting of pneumolysin from *S. pneumonia*, C5a peptidase from Group A Streptococci, hemolysin, tetanus toxoid, cholera toxin, diptheria toxoid and CRM$_{197}$. Other suitable carrier proteins are selected from the group consisting of Nontypeable *Haemophilus influenzae* (NTHi) proteins, detoxified *P. aeruginosa* toxin A, cholera toxin/toxoid, pertussis toxin/toxoid, *Clostridium perfringens* exotoxins/toxoid, hepatitis B surface antigen, hepatitis B core antigen, rotavirus VP 7 protein, and respiratory syncytial virus F and G protein.

Embodiments of the present invention are directed to antibodies, and portions thereof, which are capable of specifically binding to a repeating branched polymannose polysaccharide or to the polysaccharide portion of polysaccharide-protein conjugates, wherein said polysaccharide comprises a repeating trisaccharide unit with a structure of The antibodies are selected from the group consisting of polyclonal antibodies, monoclonal antibodies, humanized antibodies and chimeric antibodies. An embodiment of the invention also is directed to hybridoma cell lines that produce such monoclonal antibodies, humanized antibodies and chimeric antibodies. The antibodies of the invention are useful as therapeutic agents, either by themselves or in conjunction with cytotoxic or other chemotherapeutic agents, to treat *H. pylori* infections. The antibodies of the invention are useful in diagnostic and analytical assays for determining the presence of *H. pylori* polysaccharide in a test sample.

DETAILED DESCRIPTION OF THE INVENTION

Figure 1A:
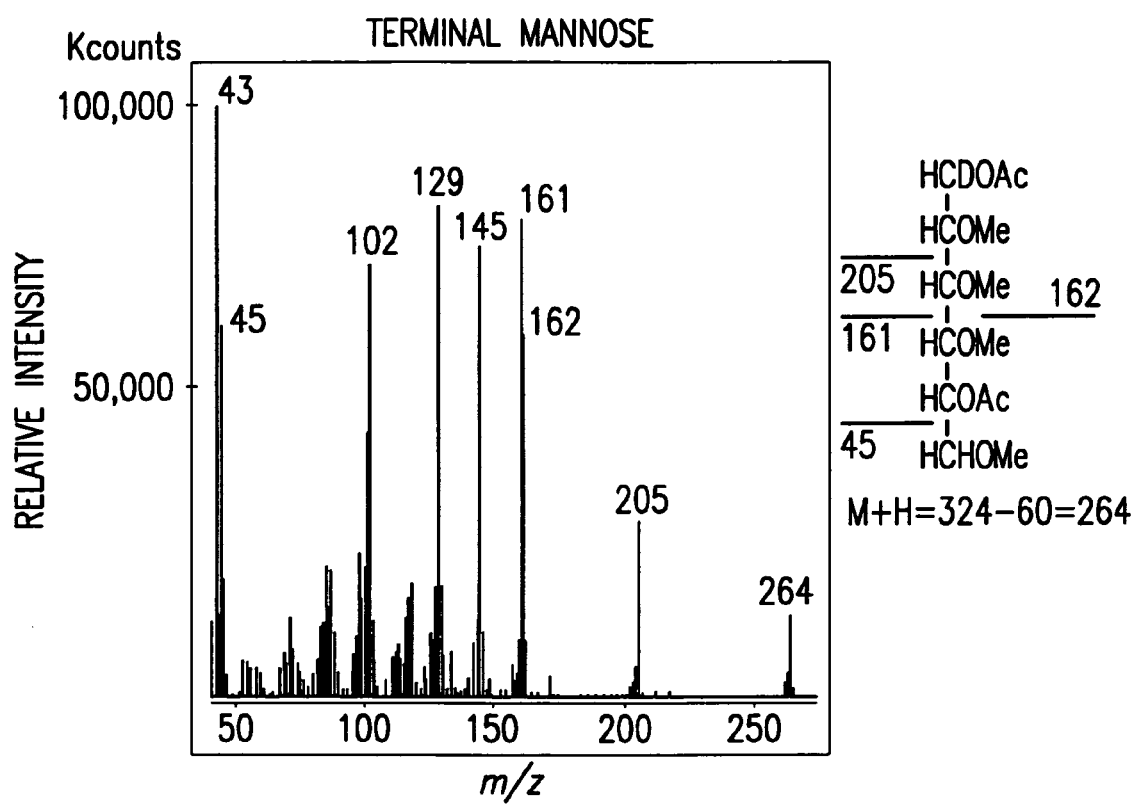
FIG. 1: This figure shows the mass-spectral fragmentation of the units that compose the polysaccharide of *H. pylori* described here, those being, unsubstituted terminal mannose (A), 2-monosubstituted mannose (B), and 2,6-disubstituted mannose (C).

Bacteria are characterized by a protective cell wall surrounding the cytoplasmic membrane. However, some species of bacteria feature a third protective covering, the glycocalyx, which is composed of polysaccharides, a class of complex carbohydrates. The glycocalyx refers to non-lipopolysaccharide associated extracellular polysaccharides. The glycocalyx is further subdivided into capsule and slime layers. In general, if the glycocalyx is stiff and tightly organized it is referred to as a capsule, and if the glycocalyx is loosely associated with the cell it is referred to as a slime layer. See Roberts, I. S. *Ann. Rev. Microbiol.* 50:285-315 (1996), the disclosure of which is hereby incorporated by reference in its entirety.

Capsules are further defined as polysaccharides that are covalently attached to either phospholipid or lipid-A molecules. Extracellular polysaccharide (EPS) molecules are released onto the cell surface with no form of attachment and are often referred to as slime layers. Distinguishing between capsule and EPS cannot be done simply on the basis of the ability of the polysaccharide to be released into the growth medium. There are unstable capsule linkages which allow polysaccharide release and there are EPS molecules that are tightly associated with the cell despite the fact that they have no apparent membrane anchoring.

The function of the glycocalyx is to prevent desiccation of the bacterial cell and to help prevent phagocytosis of the bacteria by larger microorganisms and the white blood cells of invaded host organisms. Additionally, the glycocalyx helps the bacterial cells to adhere to the host substrate and assists in warding off attacks by viruses (bacteriophages). There are some indications that elements of the glycocalyx and its associated biofilms are toxic or chemically inhibitory to hosts' defenses, thus aiding the disease mechanism. For example, it is known that in some pathogenic bacteria, such as the common *Escherichia coli* and *Streptococcus pneumoniae*, the virulence of a strain is dependent upon the function of the capsule. In contrast, non-encapsulated mutants of these prokaryotes are avirulent.

It is known that *H. pylori* produces cell-surface lipopolysaccharides (LPSs) composed of a lipid A moiety, a core oligosaccharide (OS) and an 0-chain polysaccharide (PS), however, no other *H. pylori* cell-surface carbohydrate molecule, such as a capsule or slime polysaccharide, has yet been reported. See Monteiro, M. A., *Adv. Carbohydr. Chem. Biochem.*, 57:99-158 (2001). Certain embodiments of the present invention arose from an effort to reduce extraneous polysaccharide production and allow for efficient purification of slime and capsule polysaccharides. In this effort an isogenic mutant was created by "knocking-out" the phosphoglucomutase (pgm) gene combined with extraction of the remaining glycocalyx polysaccharides.

Embodiments of the present invention describe procedures for isolating, purifying and characterizing a novel polysaccharide from *H. pylori* bacterial cells. Other embodiments are directed to methods of using the polysaccharide to produce immunogenic compositions, protein-carbohydrate conjugates and methods of immunizing mammals.

Characterization of Crude Extracts, Purified Polysaccharides

Samples are hydrolyzed at 100° C. in 6 N HCl from 4 to 48 hours prior to analysis. Reducing carbohydrate content is detected and estimated by the phenol-sulfuric acid reaction. See Dubois, M., et al., Anal. Chem. 28:350-6 (1956). Protein content is estimated by a positive reaction in the Bradford dye test. See Bradford, M., Anal. Biochem. 72:248-54 (1976). Nucleic acid content is determined by absorbance at 254 nm against a DNA standard and phosphate by a positive reaction in the method of Chen. See Chen, P. S., et al., Anal. Chem. 28:1256 (1956). Monosaccharides are individually identified by gas liquid chromatography of the trimethylsilyl derivatized monosaccharide methyl esters as described. See Chambers, R. C., et al., Biochem. J. 125:1009-18 (1971), the disclosure of which is hereby incorporated by reference in its entirety. Samples are identified by retention times compared to standards.

Isolation of Glycocalyx Polysaccharides

The crude polysaccharides, including slime, capsules and lipo-polysaccharides (LPS) are released from eighteen hour cultures of *H. pylori* strains by treatment of the cells with lysozyme in 0.04M $PO_4$/5 mM EDTA/0.02% $NaN_3$ buffer. The RNA and DNA are digested by incubation of the lysozyme treated cells with RNAse and DNAse at 37 C for 4 hrs. The crude glycocalyx polysaccharide/LPS mixture is then extracted from the cells by incubating the cell suspension in hot phenol at 70 C for 15 min. and cooled on ice bath to 2 C. After centrifugation at 5,000 rpm for 30 min. at 4 C the water phase is collected. Water (300 mL) is added to the phenol phase and hot phenol-water extraction procedure is repeated. The water phases from both extractions are combined, treated with 5 mg/ml of sodium acetate and 2× acetone (by volume) to precipitate crude polysaccharide/LPS mixture. The mixture is kept at 4 C for 3 days to complete the precipitation. The precipitated polysaccharide/LPS mixture is then collected by centrifugation (5,000 RPM for 30 min., 4° C.). The pellet is resuspended in 60 ml of water and LPS is removed by centrifugation at 60,000 rpm at 4 C for 3 hours. The polysaccharide in the supernatant is then concentrated by lyophilization, dissolved in water and fractionated by SEC on Bio-Gel P-6 (1 m×1 cm) column. The purified slime or capsule polysaccharide is collected in the high MW range and lyophilized.

Polysaccharides of may be either chemically synthesized or purified from *H. pylori*, according to conventional methods. For example, in the case of purified polysaccharides, these latter may be extracted from the microorganisms and treated to remove the toxic moieties, if necessary. A particularly useful method is described by Gotschlich et al, J. Exp. Med. (1969) 129: 1349, the disclosure of which is hereby incorporated by reference in its entirety.

Polysaccharides may be used as synthesized or purified. They may be also depolymerized or fragmented prior to use. Indeed, native capsule and slime polysaccharides often have a molecular weights of up to or above 500,000 Daltons. When it is preferred to use capsular or slime polysaccharides of lower molecular weight, e.g. 10,000 to 20,000 on average, polysaccharides as purified may be submitted to fragmentation. To this end, conventional methods are available; for example see U.S. Pat. Nos. 6,007,818 and 6,045,805 to M. Moreau, which describe a fragmentation method by reductive oxidation, the disclosures of which are hereby incorporated by reference in their entirety.

Polysaccharide Structure

Proteins can be described by referring to the N and C terminus, DNA has the 5' and 3' ends, for purposes of clarity a convention to discuss polysaccharide structures is needed. Therefore, by convention and as used herein, the "reducing end" refers to the right side of the polysaccharide molecule when looking down at the molecular representation on a page and the "non-reducing end" refers to the left side of the polysaccharide molecule when looking down at the representation on the page. See below and FIG. 2. The word reducing comes from the closing (ring) and opening (alditol) equilibrium that can occur with the monosaccharide at carbon 1 (C-1) on the right side (thus reducing end). The opening and closing equilibrium cannot occur on the left side because C-1 is fixed in position by the linkage to the next sugar on the right (man-1→2-man-1→2-mannitol).

Using the strain *H. pylori* NCTC 11637 pgm a novel polysaccharide has been isolated, purified and characterized. The compound is composed of mannose with a tandemly repeating structure as shown below:

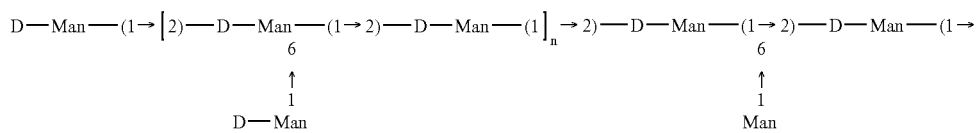

The core repeating structure is shown within the square brackets and, for clarity, an additional copy of the repeat is shown on the right, or the reducing end of the carbohydrate molecule and one additional sugar residue is shown on the left, or the non-reducing end.

The polysaccharide comprises a tandemly repeating structure where the number of repeats is given by a number "n". As defined herein, "n" refers to the number of tri-saccharide tandem repeats in a polysaccharide molecule. In one embodiment, n is an integer of less than 100. One of skill in the art will appreciate that in biological macromolecules, repeating structures are often interspersed with regions of imperfect repeats, i.e., missing branches. In addition, it is well known in the art that polysaccharides isolated and purified from natural sources such as bacteria are heterogenous in size and in branching. In this case, n may represent an average or median value for n for the molecules in a population. Therefore, in another embodiment, the value of n is between about 3 and about 100. In another embodiment, the value of n is between about 30 and about 90; alternatively, the value of n is between about 40 and about 60. In a certain embodiment, the value of n is between about 5 and about 50. In still another embodiment, the value of n is between about 10 and about 30.

The molecular weight of a single tri-saccharide repeat is about 516 Daltons. As discussed above, polysaccharides isolated and purified from natural sources are heterogenous in size. Therefore, the value for molecular weight may represent an average or median value for the molecular weight of the molecules in a particular population. In a particular embodiment, the molecular weight of the repeating polysaccharide is less than about 60,000 Daltons. In another embodiment, the molecular weight of the polysaccharide is between about 5,000 Daltons and about 60,000 Daltons. In a particular embodiment, the molecular weight of the polysaccharide is between about 15,000 Daltons and about 60,000 Daltons. In another embodiment, the molecular weight of the polysaccharide is between about 30,000 Daltons and about 45,000 Daltons. In a certain embodiment, the molecular weight of the polysaccharide is between about 5,000 Daltons and about 30,000 Daltons. In a particular embodiment, the molecular weight of the polysaccharide is between about 5,000 Daltons and about 15,000 Daltons.

Embodiments of the present invention encompass oligosaccharides. Oligosaccharides, as defined herein, refers to polysaccharides where n is between about 1 and about 5 and the length polysaccharide polymer is up to about 10 sugar residues (when the branches are not counted). For clarity, larger numbers of repeats, where n is greater than about 5 will be referred to as polysaccharides or glycocalyx polysaccharides. Oligosaccharides can prepared by either chemical synthesis from protected single residue sugars or by chemical degradation of biologically produced polysaccharides. Alternatively, oligosaccharides may be prepared by in vitro enzymatic methods.

Functional groups including hydroxyl, carboxyl, amino groups and others, may be introduced at any position in the polysaccharide upon derivatization of the native hydroxyl or carboxyl groups. Typically, as discussed later, a linker is a bifunctional molecule being able to react at one end with the hydroxyl, carboxyl or amino groups of a polysaccharide and at the other end with a carrier protein. Thus the linker provides for a functional group including, but not limited to, hydroxyl, carboxyl and amino groups. Another useful functional group that may also be introduced by the linker is a thiol group.

The polysaccharides of the present invention may be modified through chemical reactions at the functional groups. The hydroxyl, carboxyl or amino groups of the polysaccharide that are involved in linking to a carrier protein, may be native functional groups. Alternatively, they may have been introduced artificially by specific treatment. Amino groups may have been created upon controlled acidic or basic hydrolysis of native N-acyl groups e.g., N-acetyl groups.

Functional groups other than those already cited may also have been introduced upon specific treatment. For example, aldehyde groups may have been introduced all along the polysaccharide chain by periodate treatment that cleaves a carbon-carbon link between two carbon atoms bearing vicinal hydroxyl groups. When aldehyde groups are introduced all along the chain for conjugation purposes, the linker that is used, exhibits an amino group.

Use of Polysaccharides in an *H. Pylori* Immunogenic Composition

Embodiments of the present invention are directed to the polysaccharide antigens isolated and purified by the methods described herein and to methods for using such antigens. In a particular embodiment, the antigens will be used as part of an immunogenic composition to induce the production of antibodies in healthy individuals. More particularly, embodiments are directed to the use of this *H. pylori* polysaccharide as part of a to induce the production of antibodies in immunized individuals. The polysaccharide of *H. pylori* can be used as produced or isolated and purified by the methods described herein. The polysaccharide can be mixed or conjugated with other antigens, including B or T cell epitopes of other antigens.

As defined herein, "isolated" means that the polysaccharide was obtained from and separated from a particular source. For example, "isolated from *H. pylori*" means that the polysaccharide was obtained from and separated from *H. pylori* bacterial cells.

As defined herein, "purified" means that the polysaccharide of interest has been substantially separated from the various protein, lipid, and carbohydrate components that naturally occur with the polysaccharide. Whatever amounts of foreign components are in the purified polysaccharide do not interfere with the use of the purified material in a immunogenic composition or as an antigen. The term "purified" is not intended to exclude synthetic polysaccharide preparations retaining artifacts of their synthesis; nor is the term meant to exclude preparations that include some impurities, so long as the preparation exhibits reproducible polysaccharide characterization data, for example molecular weight, sugar residue content, sugar linkages, chromatographic response, and immunogenic behavior.

As defined herein, a "conjugate immunogenic composition" refers to immunogenic compositions where the immunogenic material comprises an antigenic polysaccharide that is covalently tethered to a "carrier" protein to produce a polysaccharide-protein conjugate. In one embodiment, the polysaccharide-protein conjugates of this invention can be formulated as univalent and multivalent immunogenic compositions.

As defined herein, "immunogenic material" refers to both the polysaccharide and the protein in a conjugate immunogenic composition or only the polysaccharide in a polysaccharide immunogenic composition. Generally, a polysaccharide or polysaccharide-protein conjugate immunogenic composition contains between 0.1 and 1000 μg of polysaccharide in a volume of between about 0.1 and 5 ml. In a certain embodiment of the invention, immunogenic compositions contain from about 5 to about 200 μg of immunogenic material, preferably about 10 to 50 μg, are suitable to elicit effective levels of antibody against the polysaccharide in young warm-blooded mammals. Of course, the exact dosage would be determined by routine dose/response experimentation. Several small doses given sequentially would be expected to be superior to the same amount of immunogenic composition given as a single injection. Formulations using standard methods such as those described in Remington's Pharmaceutical Sciences (Mack Publishing Co., Easton, Pa. 16th ed. (1982)) are within the scope of this embodiment of the invention.

Figure 2:
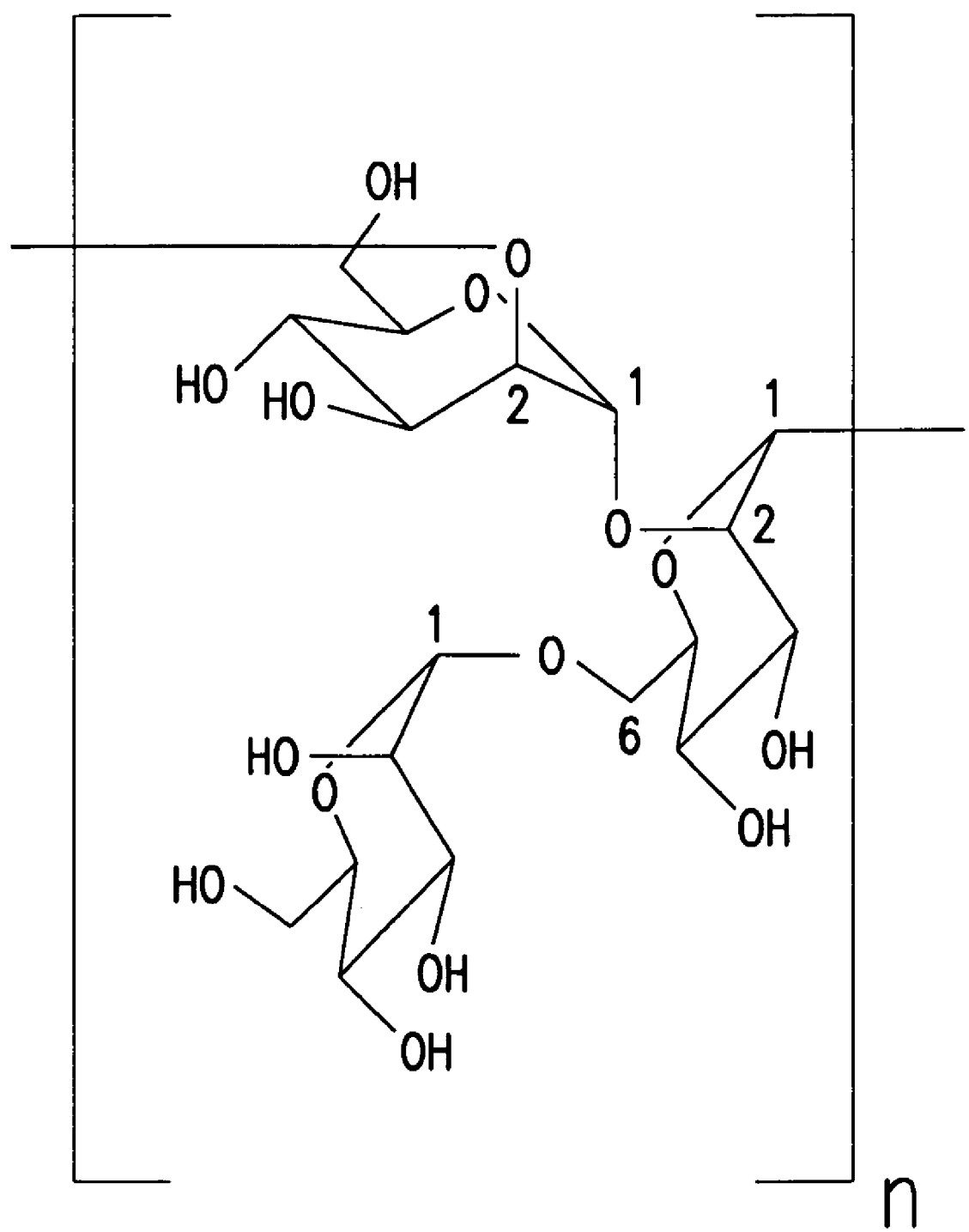
FIG. 2: This figure shows a representation of the structure of the polysaccharide that was isolated from *H. pylori* NCTC 11637 pgm LPS mutant. The structure comprises a repeating branched polysaccharide structure composed of mannose molecules.

The polysaccharides used in immunogenic compositions will have between about 5 to 100 repeating units, i.e., n in FIG. 2 will be between about 5 to about 100. In a certain embodiment, immunogenic compositions in which the polysaccharide is conjugated to protein may also be used and, for these, n should preferably between about 5 to about 50. Methods for forming conjugate immunogenic compositions are well known in the art. See, for example, Jacob, et al, Eur. J. Immunol. 16:1057-1062(1986); Parker, et al., In: Modern Approaches to Vaccines, Chanock, et al., eds, pp.133-138, Cold Spring Harbor Laboratory, Cold Spring Harbor, N.Y. (1983); Zurawski, et al., J. Immunol. 121:122-129 (1978); Klipstein, et al., Infect. Immun. 37:550-557(1982); Bessler, Immunobiol. 170:239-244(1985); Posnett, et al., J. Biol. Chem. 263:1719-1725 (1988); Ghose, et al., Molec. Immunol. 25:223-230 (1988); the disclosures of which are hereby incorporated by reference in their entirety.

One example of a conjugate immunogenic composition was developed for use against Hemophilus influenzae. See Anderson, Infec. and Immun. 39:223-238 (1983); Chu, et al., Infect. Immmun. 40:245-256 (1983); Lepow, Pediat. Infect. Dis. J. 6:804-807 (1987), the disclosures of which are hereby incorporated by reference in their entirety. Additional methods for producing a conjugate immunogenic composition are disclosed in U.S. Patents to Anderson including U.S. Pat. Nos. 4,673,574; 4,761,283; and 4,762,713: U.S. patents to Anderson and Eby including U.S. Pat. Nos. 4,902,506; 5,097,020; and 5,360,897 and European Patent No. 245,045: U.S. patents to Frank, et al., including U.S. Pat. No. 4,789,735; European Patent Publication No.206,852: U.S. patent to Gordon, including U.S. Pat. No. 4,619,828: U.S. patent to Beachey including U.S. Pat. No. 4,284,537: and in see in particular W. E. Dick and M. Beurret, Glycoconjugates of Bacterial Carbohydrate Antigens vol.10, pages 48-114 in Conjugate Vaccines, Eds. J. M. Cruse and R. E. Lewis Jr. (Contributions to Microbiology and Immunology: vol.10), Karger Publishing, Basel (1989), all of which, the disclosures of which are hereby incorporated by reference in their entirety.

Suitable diluents or carrier media for formulating an immunogenic composition include sodium phosphate-buffered saline (pH 7.4) of 0.125M aluminum phosphate gel suspended in sodium phosphate-buffered saline at pH 6 and other conventional media. Other pharmaceutical diluents suitable for use in immunogenic compositions are known in the art.

Immunogenic compositions will generally be designed for parenteral administration, although the present invention is compatible with other forms of administration as well. Immunization procedures will typically involve at least one and up to five inoculations with an immunogenic composition. A typical course of immunization involves 3 inoculations separated by intervals of 3 to 10 weeks. There are procedures for optimizing inoculation schedules and the other parameters associated with immunization and these are well known in the art.

The immunogenic compositions of the invention may be administered by injection to warm-blooded mammals of any age and are especially adapted to induce active immunization against systemic infections in young mammals caused by $H. pylori$.

Multivalent Immunogenic Compositions

For the synthesis of a monovalent conjugate immunogen, polysaccharides derived from a single serotype of bacterium may be conjugated to protein. For the synthesis of a multivalent conjugate immunogenic composition, polysaccharide-protein conjugates may be produced by conjugating a mixture of polysaccharides purified from bacteria of two different species to a carrier protein. Alternatively, a multivalent conjugate immunogenic composition may be produced by combining polysaccharides purified from bacteria of two or more different serotypes of the same bacteria and conjugating them as a mixture to a carrier protein. Alternatively, polysaccharide-protein conjugates produced by reacting a single type of polysaccharide with carrier protein in separate reactions using different polysaccharides, may be mixed. Thus, a multivalent immunogenic composition may comprise a carrier protein bearing a homogeneous or a heterogeneous population of linked polysaccharides.

Polysaccharide-Protein Conjugates

As defined herein, a "polysaccharide-protein conjugate" refers to polysaccharide molecules conjugated to protein carrier molecules through one or more covalent bonds. Conjugation may be direct, where the atoms from the polysaccharide are covalently bonded to atoms from the protein surface. Conjugation may be through a linker molecule, which reacts with both the polysaccharide and the protein and connects the two and tethers the carbohydrate to the protein.

Direct Polysaccharide to Protein Conjugation

Conjugates of the polysaccharide and protein carriers are formed by reacting reducing end groups of the polysaccharide polymer fragment to primary amino groups of a carrier protein to yield antigenic determinants of the polymer covalently linked to the carrier protein. The reducing groups may be formed by selective hydrolysis or specific oxidative cleavage of the carbohydrate, or combinations of both.

Many methods of conjugation are known in the art, such as, for conjugating a polysaccharide to a protein. In general, the polysaccharide should be activated or otherwise rendered amenable to conjugation, i.e., at least one moiety must be rendered capable of covalently bonding to a protein or other molecule. For instance, U.S. Pat. No.4,356,170, issued to Jennings, describes the use of periodic acid to generate aldehyde groups on the polysaccharide and then performs reductive amination using cyanoborohydride. U.S. Pat. No. 4,663,160, issued to Tsay et al., also used periodic acid to generate aldehyde groups but then linked the polysaccharide to a protein derivatized with a 4-12 carbon moiety (prepared in the presence of a condensing agent) with a Schiff's base reaction in the presence of a reducing agent such as cyanoborohydride. U.S. Pat. No. 4,619,828, issued to Gordon, used cyanogen bromide to activate the polysaccharide and then conjugated it through a spacer bridge of 4-8 carbon atoms to the protein. Still other methods of conjugation are known in the art.

Where the polysaccharide is hydrolyzed to form polysaccharide fragments having only one functional aldehyde group, conjugation to a multifunctional protein (having at least two free amine groups) results in a conjugate in which a single molecule of the protein has one or more polysaccharide fragments covalently attached. As used herein, the terms "polysaccharide" or "polysaccharide fragments" will be used interchangeably in the context of conjugation reactions. It can readily be seen that the number of polysaccharides attached to the protein can be routinely regulated by changes in the conditions of the conjugation reaction, including the relative concentration of polysaccharide or polysaccharide fragments to protein and the overall concentration of the reactants. Of course, regulation of any reaction parameter, e.g., time, temperature, pH, etc., which affects the reactivity or rate of reaction will alter the final composition and structure of the conjugate.

When the polysaccharide fragment has at least one functional aldehyde group located on each end of the fragment, conjugation to a multifunctional protein can result in several types of conjugate. For example, conjugation of such reactants has the potential for forming a lattice or network structure, particularly where there are many free amines on the protein and capsular fragments are in low molar excess to protein. The degree of crosslinking and overall size of the network or lattice can be regulated by routine variation of the conditions of the conjugation reaction.

In one embodiment, the conjugation is carried out according to the reductive amination process of Schwartz and Gray, Arch. Biochem. Biophys. 181: 542-549 (1977); and in Anderson and Eby U.S. Pat. Nos. 4,902,506; 5,097,020; and 5,360,897 the disclosures of which are hereby incorporated by reference in their entirety. Briefly, the process involves reacting the reducing polysaccharide fragment and carrier protein in the presence of cyanoborohydride ions, or another reducing agent which will not reduce the reducing ends of interest nor adversely affect the carrier protein or polysaccharide.

The cyanoborohydrate ions (or their equivalent) act primarily as a mild selective reducing agent of the Schiff base intermediate formed between the carbonyl groups of the polysaccharide fragment and amino groups of the protein. A secondary effect of such ions is the slower reduction of any active aldehyde groups remaining on the polysaccharide fragments after conjugation has occurred. Optionally, after conjugation, additional cyanoborohydrate ions (or their equivalent) may be added to reduce such unreacted free aldehyde groups. It is often desirable to add the stronger reducing agent, borohydride ion, after conjugation to ensure adequate reduction of the remaining carbonyl groups.

Carrier Proteins

As is well known in the art, a given polysaccharide antigen may vary in its immunogenicity. It is often necessary or desirable to conjugate the polysaccharide to a protein from another species known to be immunogenic in the target host. As defined herein, such a foreign protein is referred to as a "carrier protein". Carrier proteins serve to enhance the antigenicity and immunogenicity of the polysaccharide antigen. As used herein, the term "carrier effect" refers to the process where the antigenicity and immunogenicity of a weakly immunogenic or non-immunogenic molecule is enhanced, by being attached to a more immunogenic molecule as carrier (e.g., a heterologous protein). In this case, the polysaccharide in the combined polysaccharide-protein conjugate becomes more immunogenic than if it were presented alone. Carrier proteins contain T cell epitopes for stimulating T-cell help for producing antibody responses.

Suitable carrier proteins are those that are safe for administration to young mammals and immunologically effective as carriers. Safety would include absence of primary toxicity and minimal risk of allergic complications. Diphtheria and tetanus toxoids are examples of carrier proteins that fulfill these criteria; that is, suitably prepared, they are non-toxic and the incidence of allergic reactions is well documented. Though the risk of allergic reaction may be relatively significant for adults, it is minimal for infants.

If an animal is previously immunized with the carrier alone, it may become "primed" for an enhanced response not only to the carrier antigen but also the attached weaker antigen. Infants are routinely immunized with tetanus and diphtheria toxoids. Thus, they would be primed for subsequent presentation of a capsular polymer antigen conjugated to either of these toxoids.

Cross-reacting materials or CRMs are especially useful for some embodiments of the present invention. One may produce genetically altered proteins, which are antigenically similar to the certain bacterial toxins, yet non-toxic. These are called "cross reacting materials", or CRMs. $CRM_{197}$ is noteworthy since it has a single amino acid change from the native diphtheria toxin and is immunologically indistinguishable from it. See Pappenheimer et al., Immunochem., 9:891-906, (1972), and U.S. Pat. No. 5,614,382 the disclosures of which are hereby incorporated by reference in their entirety. CRM3201 is a genetically manipulated variant of pertussis toxin. See Black et al., Science, 240:656-659, (1988), the disclosures of which is hereby incorporated by reference in their entirety.

When the polysaccharide of *H. pylori* is used as the immunogen it can be conjugated to an immunogenic carrier protein. Conjugation of the extracellular polysaccharide of *H. pylori* to an immunogenic carrier protein can enhance or modify the immunogenicity of the polysaccharide. Preferred carrier proteins include pneumolysin from *S. pneumonia* (wild-type or mutant with reduced toxicity, such as those described in U.S. Pat. No. 5,565,204, European Patent Number 449,856 and Published International Patent Application Number WO 90/06951, the disclosures of which are hereby incorporated by reference in their entirety), C5a peptidase from Group A Streptococci, hemolysin from *Staphylococcal aureus*, tetanus toxoid, cholera toxin or toxoid (such as those described in Published International Patent Application Numbers WO 00/18434, WO 02/098368, and WO 02/098369, the disclosures of which are hereby incorporated by reference in their entirety), diptheria toxoid and $CRM_{197}$. Other suitable carrier proteins are selected from the group consisting of Nontypeable *Haemophilus influenzae* (NTHi) proteins, detoxified *P. aeruginosa* toxin A, pertussis toxin/toxoid, *Clostridium perfringens* exotoxins/toxoid, hepatitis B surface antigen, hepatitis B core antigen, rotavirus VP 7 protein, and respiratory syncytial virus F and G protein.

Polysaccharide-Protein Conjugates: Using Linkers

Success with the direct conjugation depends on how many surface groups are available to each reaction partner. Steric effects are known to influence the efficiency of conjugation of polysaccharides to protein. This can be overcome using highly flexible bifunctional linkers or spacer arms (linkers) to access otherwise inaccessible sites on the protein being conjugated. Linkers do not have any unified classification scheme, however the following characteristics are common: they are low molecular weight, bifunctional reagents capable of stepwise or simultaneous reactions with selected functional groups on the polysaccharide and protein. The bacterial polysaccharides can have a wide array of functional groups like hydroxyl groups, amino groups, which may or may not be acylated, phosphodiesters and carboxyl groups. Any of these functional groups, in principle, can be used for coupling of the linker to polysaccharide. Various reviews dealing with synthesis of glycoconjugates can be found in the literature. See Dick, W. E., and Beurret, M. (1989). *Glycoconjugates of bacterial carbohydrate antigens*. In "Contributions to Microbiology and Immunology" (J. M. Crause and R. E.Lewis, Jr. eds.) Vol.10, pp.48-114. S. Kager, Basel), the disclosure of which is hereby incorporated by reference in its entirety.

As discussed above, polysaccharides may be conjugated to carrier proteins through an intermediary or spacer molecule known as a linker. For example, according to the methods provided herein, reductive amination of the reducing end of an polysaccharide is performed using a molecule containing two amino groups. In a certain embodiment of the invention, reductive amination is accomplished by reacting a given molar amount of polysaccharide with a diaminoethane solution in 10× molar excess in 0.2M $KH_2 PO_4$ at about pH=9 at a temperature of approximately 25-100° C., and preferably 100° C. for between about 1-60 minutes, and preferably about 15 minutes. Thereafter, a molar amount of pyridine borane equivalent to 25 times the molar concentration of polysaccharide in the preparation may be added, and the reaction is performed at between about 25-100° C., and preferably about 50° C. for between about 1 and 72 hours, preferably about 48 hours.

The resulting product of the reductive amination reaction may then be reacted with a "linker". As defined herein, a "linker" is a bifunctional molecule, wherein both functional groups are capable of reaction with either the terminal amino group of the activated polysaccharide or amino groups present in the structure of the carrier protein, such that the bifunctional molecule may serve to link together the polysaccharide and the carrier protein. In a particular embodiment of the invention, the bifunctional group is a diester, and is, more particularly, a diester of adipic acid, which has been shown to be associated with more efficient glycosylation of protein. In a specific embodiment of the invention a polysaccharide, having been subjected to reductive amination as described supra, is further reacted with a succinimidyl diester of succinic or, more preferably, adipic acid; this reaction may best be performed with the aminated polysaccharide at a molar concentration (as amino groups) equivalent to about one-fifth of the molar concentration of succinimidyldiester of adipic acid (SIDEA) or succinimidyidiester of succinic acid (SIDES) in a solution of dimethylsulfoxide (DMSO) at between about 0° C. and about 25° C., and preferably about 4° C. for between about 0.5 and 5 hours and preferably about 2 hours. The activated polysaccharide may then be collected by precipitation using 1, 4 dioxane (80% v/v), which also leaves in the supernatant the excess of SIDEA (or SIDES).

In a specific embodiment of the invention, activated polysaccharides may be linked to $CRM_{197}$ protein which has been purified as follows: $CRM_{197}$, produced by the strain *Corynebacterium diphtheriae*, may be separated from culture medium by passing the bacterial culture through a Millipore membrane, thereby precipitating protein from the filtrate, and then purifying $CRM_{197}$ by ion exchange chromatography. Alternatively, substantially pure $CRM_{197}$ may be obtained by any method known in the art.

Activated polysaccharide may be covalently linked to carrier protein in the presence of an organic solvent and, optionally, any other agent (such as a condensing agent) in order to promote the linkage of the terminal functional group of the activated polysaccharide to the protein.

In a certain embodiment of the invention, activated polysaccharide bearing a terminal ester group may be covalently linked to free amino groups present on carrier protein as follows: Activated polysaccharide may be dissolved in dimethylsulfoxide and then added to an aqueous solution of carrier protein (for example, but not limited to $CRM_{197}$ at a concentration of about 2 mg/ml) such that the molar ratio of monoester-activated polysaccharide/total amino groups of the carrier protein is about 1:2 and the final concentration of DMSO is about 50% v/v. The conjugation reaction is performed at 4° C. and although the reaction is near to completion in about 2 hours, it is suitable to leave the reaction going overnight in order to increase the yield of reaction at the highest values for each type specific glycoconjugate. The glycoconjugates so obtained are then purified by gel chromatography.

Linkers

The use of linkers is well known in the field of conjugate immunogenic compositions. See Dick et aL, Conjugate Vaccines, J. M. Cruse and R. E. Lewis, Jr., eds., Karger, N.Y., vol. 10 pp. 48-114, (1989) the entire contents of which are hereby incorporated by reference in their entirety. Linking a polysaccharide to a carrier protein may be accomplished, for example, by using the cross linking reagent such as glutaraldehyde. However, in a certain embodiment, the polysaccharide and the protein carrier are separated by a linker. The linker promotes optimum immunogenicity of the conjugate and more efficient coupling of the polysaccharide with the carrier. Linkers separate the two antigenic components by chains whose length and flexibility can be adjusted as desired. Between the bifunctional sites, the chains can contain a variety of structural features, including heteroatoms and cleavage sites. Linkers also permit corresponding increases in translational and rotational characteristics of the antigens, increasing access of the binding sites to soluble antibodies. Besides adipic acid dihydrazide (ADH), suitable linkers include, for example, heterodifunctional linkers such as epsilon-aminohexanoic acid, 3-(2-pyridyidithio propionyl hydrazide (PDPH), chlorohexanol dimethyl acetal, D-glucuronolactone and p-nitrophenyl amine. Coupling reagents contemplated for use include hydroxysuccinimides and carbodiimides. Many other linkers and coupling reagents known to those of ordinary skill in the art are also suitable for use. Such compounds are discussed in detail by Dick et al. See Dick et al., Conjugate Vaccines, J. M. Cruse and R. E. Lewis, Jr., eds., Karger, N.Y., pp. 48-114, the entire contents of which are hereby incorporated by reference.

Where a carrier and one or more antigens such as a polysaccharide are conjugated (i.e., covalently associated), conjugation may be by any chemical method, process or genetic technique commonly used in the art. For example, a carrier polypeptide and one or more antigens selected from a group comprising a carbohydrate, an oligosaccharide, a lipid, a lipooligosaccharide, a polysaccharide, an oligosaccharide-protein conjugate, a polysaccharide-protein conjugate, a peptide-protein conjugate, an oligosaccharide-peptide conjugate, a polysaccharide-peptide conjugate, a protein-protein conjugate, a lipooligosaccharide-protein conjugate, a polysaccharide-protein conjugate, or any combination thereof, may be conjugated by techniques, including, but not limited to: (1) direct coupling via protein functional groups (e.g., thiol-thiol linkage, amine-carboxyl linkage, amine-aldehyde linkage; enzyme direct coupling); (2) homobifunctional coupling of amines (e.g., using bis-aldehydes); (3) homobifunctional coupling of thiols (e.g., using bis-maleimides); (4) homobifunctional coupling via photoactivated reagents (5) heterobifunctional coupling of amines to thiols (e.g., using maleimides); (6) heterobifunctional coupling via photoactivated reagents (e.g., the β-carbonyidiazo family); (7) introducing amine-reactive groups into a poly- or oligosaccharide via cyanogen bromide activation or carboxymethylation; (8) introducing thiol-reactive groups into a poly- or oligosaccharide via a heterobifunctional compound such as maleimido-hydrazide; (9) protein-lipid conjugation via introducing a hydrophobic group into the protein and (10) protein-lipid conjugation via incorporating a reactive group into the lipid. Also, contemplated are heterobifunctional "non-covalent coupling" techniques such the Biotin-Avidin interaction. For a comprehensive review of conjugation techniques, see Aslam and Dent, *Bioconjugation: Protein Coupling Techniques for the Biomedical Sciences*, Macmillan Reference Ltd., London, England, 1998, the disclosure of which is hereby incorporated by reference in its entirety.

Other methods well known in the art for effecting conjugation of oligosaccharides and polysaccharides to immunogenic carrier proteins are also within the scope of some embodiments of the invention. Such methods are described in, for example, U.S. Pat. Nos. 5,153,312 and 5,204,098; EP 0 497 525; and EP 0 245 045, the entire disclosures of which are hereby incorporated by reference.

Immunogenic Compositions

In certain embodiments, the present invention provides immunogenic compositions that comprise at least one *H. pylori* polysaccharide, immunogenic portion thereof, an epitope thereof, a polysaccharide-protein conjugate thereof, immunogenic material thereof or biological equivalent thereof. More specifically, these compositions comprise at least one polysaccharide comprising a structure as shown in FIG. 2. In other embodiments, the compositions comprise at least one a polysaccharide-protein conjugate thereof, immunogenic material thereof or biological equivalent thereof as well as an antibody that immunospecifically binds to any of the foregoing *H. pylori* polysaccharides, immunogenic portions thereof, or epitopes thereof.

The formulation of such immunogenic compositions is well known to persons skilled in this field. In one embodiment, immunogenic compositions of the invention include a pharmaceutically acceptable diluent and/or pharmaceutically acceptable carriers. Such pharmaceutically acceptable carriers are not to be confused with "carrier proteins", which are used in attaching the carbohydrate of the invention to a protein and, which modify the immune response to that carbohydrate. To avoid confusion with the protein carriers herein described, the term pharmaceutically acceptable diluent will be preferred over pharmaceutically acceptable carriers, but these terms may occasionally be used interchangeably. Suitable pharmaceutically acceptable diluents include any and all conventional solvents, dispersion media, fillers, solid carriers, aqueous solutions, coatings, antibacterial and antifungal agents, isotonic and absorption delaying agents, and the like. Suitable pharmaceutically acceptable diluents include, for example, one or more of sterile water, water for injection (WFI), sterile isotonic saline, phosphate buffered saline, dextrose, glycerol, ethanol and the like, as well as combinations thereof. Pharmaceutically acceptable diluents may further comprise minor amounts of auxiliary substances such as wetting or emulsifying agents, preservatives or buffers, which enhance the shelf life or effectiveness in the body. The preparation and use of pharmaceutically acceptable diluents is well known in the art. Except insofar as any conventional media or agent is incompatible with the active ingredient, use thereof in the immunogenic compositions of the present invention is contemplated.

In certain embodiments, the immunogenic composition will comprise one or more adjuvants. As used herein, an "adjuvant" is a substance that serves to enhance the immunogenicity of an immunogenic composition of particular embodiments of the invention.

A number of cytokines or lymphokines have been shown to have immune modulating activity, and thus may be used as adjuvants, including, but not limited to, the interleukins 1-$\alpha$, 1-$\beta$, 2, 4, 5, 6, 7, 8, 10, 12 (see, e.g., U.S. Pat. No. 5,723,127), 13, 14, 15, 16, 17 and 18 (and its mutant forms), the interferons-$\alpha$, $\beta$ and $\gamma$, granulocyte-macrophage colony stimulating factor (see, e.g., U.S. Pat. No. 5,078,996 and ATCC Accession Number 39900), macrophage colony stimulating factor, granulocyte colony stimulating factor, GSF, and the tumor necrosis factors a and $\beta$. Still other adjuvants useful in particular embodiments of the invention include a chemokine, including without limitation, MCP-1, MIP-1$\alpha$, MIP-1$\beta$, and RANTES. Adhesion molecules, such as a selectin, e.g., L-selectin, P-selectin and E-selectin may also be useful as adjuvants. Still other useful adjuvants include, without limitation, a mucin-like molecule, e.g., CD34, GlyCAM-1 and MadCAM-1, a member of the integrin family such as LFA-1, VLA-1, Mac-1 and p150.95, a member of the immunoglobulin superfamily such as PECAM, ICAMs, e.g., ICAM-1, ICAM-2 and ICAM-3, CD2 and LFA-3, co-stimulatory molecules such as CD40 and CD40L, growth factors including vascular growth factor, nerve growth factor, fibroblast growth factor, epidermal growth factor, B7.2, PDGF, BL-1, and vascular endothelial growth factor, receptor molecules including Fas, TNF receptor, Flt, Apo-1, p55, WSL-1, DR3, TRAMP, Apo-3, AIR, LARD, NGRF, DR4, DR5, KILLER, TRAIL-R2, TRICK2, and DR6. Still another adjuvant molecule includes Caspase (ICE). See, also International Patent Publication Nos. WO98/17799 and WO99/43839, the disclosures of which are incorporated herein by reference in their entirety.

Suitable adjuvants used to enhance an immune response further include, without limitation, MPL™ (3-O-deacylated monophosphoryl lipid A; Corixa, Hamilton, Mont.), which is described in U.S. Pat. No. 4,912,094, which is hereby incorporated by reference. Also suitable for use as adjuvants are synthetic lipid A analogs or aminoalkyl glucosamine phosphate compounds (AGP), or derivatives or analogs thereof, which are available from Corixa (Hamilton, Mont.), and which are described in U.S. Pat. No. 6,113,918, which is hereby incorporated by reference. One such AGP is 2-[(R)-3-Tetradecanoyloxytetradecanoylamino] ethyl 2-Deoxy-4-O-phosphono-3-O-[( R)-3-tetradecanoyoxytetradecanoyl]-2-[( R)-3-tetradecanoyloxytetradecanoyl-amino]-b-D-glucopyranoside, which is also known as 529 (formerly known as RC529). This 529 adjuvant is formulated as an aqueous form or as a stable emulsion.

Still other adjuvants include mineral oil and water emulsions, aluminum salts (alum), such as aluminum hydroxide, aluminum phosphate, etc., Amphigen, Avridine, L121/ squalene, D-lactide-polylactide/glycoside, pluronic polyols, muramyl dipeptide, killed Bordetella, saponins, such as Stimulon™ QS-21 (Antigenics, Framingham, Mass.), described in U.S. Pat. No. 5,057,540, which is hereby incorporated by reference, and particles generated therefrom such as ISCOMS (immunostimulating complexes), Mycobacterium tuberculosis, bacterial lipopolysaccharides, synthetic polynucleotides such as oligonucleotides containing a CpG motif (U.S. Pat. No. 6,207,646, which is hereby incorporated by reference), a pertussis toxin (PT), or an E. coli heat-labile toxin (LT), particularly LT-K63, LT-R72, PT-K9/G129; see, e.g., International Patent Publication Nos. WO 93/13302 and WO 92/19265, incorporated herein by reference.

Also useful as adjuvants are cholera toxins and mutants hereof, including those described in published International Patent Application number WO 00/18434 (wherein the glutamic acid at amino acid position 29 is replaced by another amino acid (other than aspartic acid), preferably a histidine). Similar CT toxins or mutants are described in published International Patent Application number WO 02/098368 (wherein the isoleucine at amino acid position 16 is replaced by another amino acid, either alone or in combination with the replacement of the serine at amino acid position 68 by another amino acid; and/or wherein the valine at amino acid position 72 is replaced by another amino acid). Other CT toxins are described in published International Patent Application number WO 02/098369 (wherein the arginine at amino acid position 25 is replaced by another amino acid; and/or an amino acid is inserted at amino acid position 49; and/or two amino acids are inserted at amino acid positions 35 and 36).

A variety of administration routes are available. The particular mode selected will depend, of course, upon the particular immunogenic composition selected, the particular condition being treated, and the dosage required for therapeutic efficacy. The methods of certain embodiments of this invention, generally speaking, can be practiced using any mode of administration that is medically acceptable, meaning any mode that produces effective levels of an immune response without causing clinically unacceptable adverse effects. Examples of routes of administration include, but are not limited to, parenteral (e.g., intravenous, intraarterial, intradermal, transdermal, intramuscular, subcutaneous, intraperitoneal), transmucosal (e.g., oral, rectal, intranasal, vaginal, respiratory) and transdermal (topical).

The preferred method of administration of the immunogenic composition is parenteral administration. Solutions or suspensions used for parenteral administration include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Immunogenic compositions suitable for injectable use include sterile aqueous solutions (where water soluble) or dispersions and sterile powders for the extemporaneous preparation of sterile injectable solutions or dispersion. In all cases, the composition must be sterile and should be fluid to the extent that easy syringability exists. The composition must be stable under the conditions of manufacture and storage and must be preserved against the contaminating action of microorganisms such as bacteria and fungi. The carrier is a solvent or dispersion medium containing, for example, water, ethanol, polyol (e.g., glycerol, propylene glycol, and liquid polyethylene glycol, and the like), and suitable mixtures thereof. The proper fluidity is maintained, for example, by the use of a coating such as lecithin, by the maintenance of the required particle size in the case of a dispersion and by the use of sdrfactants. Prevention of the action of microorganisms is achieved by various antibacterial and antifungal agents, for example, parabens, chlorobutanol, phenol, ascorbic acid, and the like. In many cases, it is preferable to include isotonic agents, for example, sugars, polyalcohols such as mannitol, sorbitol, and sodium chloride in the composition. Prolonged absorption of the injectable compositions is brought about by including in the composition an agent which delays absorption, for example, aluminum monostearate and gelatin.

Sterile injectable solutions are prepared according to one embodiment by incorporating a polysaccharide or polysaccharide-protein conjugate of this invention in the required amount in an appropriate solvent with one or a combination of ingredients provided above, as required, followed by filtered sterilization. Generally, dispersions are prepared by incorporating the active compound into a sterile vehicle that contains a basic dispersion medium and the required other ingredients from those provided above. In the case of sterile powders for the preparation of sterile injectable solutions, the preferred methods of preparation are vacuum-drying and freeze-drying which yields a powder (or "cake") of the active ingredient plus any additional desired ingredient from a previously sterile-filtered solution thereof.

The compositions can be conveniently presented in unit dosage form and can be prepared by any of the methods well known in the art of pharmacy. All methods include the step of bringing the polysaccharide into association with a diluent that constitutes one or more accessory ingredients. In general, the compositions are prepared by uniformly and intimately bringing the immunogenic agent into association with a liquid diluent, a finely divided solid carrier, or both, and then, if necessary, shaping the product.

Other delivery systems can include time-release, delayed release or sustained release delivery systems. Many types of delivery systems are available and known to those of ordinary skill in the art. They include polymer based systems such as polylactic and polyglycolic acid, polyanhydrides and polycaprolactone; nonpolymer systems that are lipids including sterols such as cholesterol, cholesterol esters and fatty acids or neutral fats such as mono-, di- and triglycerides; hydrogel release systems; silastic systems; peptide based systems; wax coatings, compressed tablets using conventional binders and excipients, partially fused implants and the like.

In particular embodiments, the immunogenic material of the present invention may be administered as the sole active immunogen in an immunogenic composition, or alternatively, the composition may include other active immunogens to provide a multivalent composition, including other immunogenic polysaccharides, lipopolysaccharides, lipooligosaccharides, polypeptides, or immunologically-active proteins of one or more other microbial pathogens (e.g., virus, prion, bacterium, or fungus, without limitation). The compositions may comprise one or more desired polysaccharides, proteins, polysaccharide-protein conjugates, fragments or pharmaceutical compounds as desired for a chosen indication. In the same manner, the compositions may also include nucleic acids which encode the same diverse group of proteins.

Certain embodiments of the present invention contemplate multivalent immunization regimens wherein any composition useful against a pathogen can be combined therein or therewith the compositions of the present invention. For example, without limitation, in a particular embodiment, a patient can be administered the immunogenic composition of the present invention and another immunogenic composition for immunizing against streptococcus, as part of a multivalent immunization regimen. Persons of skill in the art would be readily able to select immunogenic compositions for use in conjunction with the immunogenic compositions of the present invention for the purposes of developing and implementing multivalent immunization regimens.

Embodiments of the present invention also relate to methods of inducing an immune response in a mammal comprising the step of administering to the mammal an immunogenic composition of this invention. The immunogenic composition is a composition which is both antigenic and immunogenic in the treated animal or human such that an immunologically effective amount of the immunogenic agent(s) contained in such composition brings about the desired immune response against *H. pylori* infection. Preferred embodiments relate to a method for the treatment, including amelioration, or prevention of *H. pylori* infection in a human comprising administering to a human an immunologically effective amount of the composition.

The phrase "immunologically effective amount" as used herein refers to the administration of that amount to a mammalian host (preferably human), either in a single dose or as part of a series of doses, sufficient to at least cause the immune system of the individual treated to generate a response that reduces the clinical impact of the infection. The dosage amount can vary depending upon specific conditions of the individual, such as, for example, body weight or immune status. This amount can be determined in routine trials or otherwise by means known to those skilled in the art.

Methods of Detecting Past and Present *H. Pylori* Infections

According to a further embodiment of the present invention, a method is provided for diagnosing *H. pylori* infection in a mammal comprising: (i) isolating a polysaccharide from *H. pylori*, wherein said polysaccharide comprises a repeating trisaccharide unit with a structure as shown in FIG. 2, wherein n is an integer of less than 100; (ii) producing a monoclonal antibody that specifically recognizes and binds to said polysaccharide; (iii) reacting said monoclonal antibody with gastric fluid including saliva of patients potentially infected with *H. pylori*; and (iv) detecting the presence of antibody bound to *H. pylori* polysaccharide.

In another embodiment, the invention comprises a method of detecting whether an individual has been infected with or exposed to *H. pylori* comprising: (i) isolating a polysaccharide from *H. pylori*, wherein said polysaccharide comprises a repeating trisaccharide unit with a structure as shown in FIG. 2, wherein n is an integer of less than 100; (ii) reacting antibodies obtained from a potentially infected subject with said polysaccharide; and (iii) detecting whether antibodies from a potentially infected subject recognize and bind to said polysaccharide.

One embodiment of the invention relates to a kit or set for the detection and/or the identification of bacteria belonging to the species *H. pylori* or to a related microorganism, or for the detection and/or the identification of a microorganism characterized in that it comprises a polysaccharide according to the invention.

Certain embodiments of the invention provide methods for the detection and/or the identification of bacteria belonging to the species *Helicobacter pylori* or to related microorganisms in a biological sample, characterized in that it produces a polysaccharide as described herein.

There are embodiments of the invention that encompass kits for detecting the presence of *H. pylori* in a biological sample. For example, the kit comprises reagents such as a labeled or labelable compound or agent such as a monoclonal antibody capable of detecting *H. pylori* polysaccharide in a biological sample; means for determining the amount of *H. pylori* polysaccharide in the sample; and means for comparing the amount of *H. pylori* polysaccharide in the sample with a standard. The compound or agent is packaged in a suitable container. The kit further comprises instructions for using the kit to detect *H. pylori* polysaccharide.

Antibodies Immunoreactive with *Helicobacter Pylori* Polysaccharides

In still another embodiment, the present invention provides antibodies immunoreactive with the *H. pylori* polysaccharides. Exemplary antibodies include polyclonal antibodies, monoclonal antibodies, humanized antibodies, bispecific antibodies, and heteroconjugate antibodies. Antibodies may be generated in animals using this polysaccharide and then used in assays for detecting antigens indicative of *H. pylori* infection from the gastric fluids of potentially infected subjects.

Antibody responses to tandem repeat structures such as the polysaccharide of the present invention, exhibit some unique features. First, the regularity of the repeating units means that antigen molecules of vastly different molecular weights can bind to antibodies specific for the polysaccharide. Second, the repeat structures of the larger length polysaccharides are capable of inducing T-cell independent antibody responses. Therefore, when using polysaccharides conjugated to protein carriers having T-cell helper epitopes, both T-cell independent and T-cell dependent antibody responses can be stimulated. Therefore, immune response can be modified by appropriate selection of polysaccharide size and whether or not a carrier protein is used.

Polyclonal Antibodies

In certain embodiments, the anti-polysaccharide antibodies are polyclonal antibodies. Polyclonal antibodies, as defined herein, refers to a mixture of antibodies having differing specificities derived from a preparation of serum and originating from different B-cell clones. The preparation and characterization of polyclonal antibodies are well known in the art. See, e.g., Antibodies "A Laboratory Manual", E. Harlow and D. Lane, Cold Spring Harbor Laboratory Press, 1988, the disclosure of which is hereby incorporated by reference in its entirety.

Polyclonal antibodies are raised in a mammal, for example, by administering one or more injections of an immunogen or immunogenic material and, if desired, an adjuvant. Typically, the immunogen or immunogenic material with or without the adjuvant is injected in the mammal by multiple subcutaneous or intraperitoneal injections. The immunogenic material may include the Helicobacter pylon polysaccharide, the polysaccharide-protein conjugate or a larger assembly of immunogens. Usually, beginning 2-6 weeks after the first immunization, blood is collected from the immunized animal, allowed to clot and serum is harvested. The serum contains the anti-polysaccharide polyclonal antibodies from the immunized animal and is often referred to as anti-sera. A wide range of animal species is used for the production of specific anti-sera. Typically an animal used for production of anti-polysaccharide polyclonal anti-sera is a rabbit, a mouse, a rat, a hamster or a guinea pig. Under some circumstances, a horse, goat, sheep or other large mammal is used to generate anti-polysaccharide polyclonal antisera.

Monoclonal Antibodies

The anti-polysaccharide polypeptide monoclonal antibodies are readily prepared through use of well-known hybridoma techniques such as those exemplified in U.S. Pat. No. 4,196,265, to H. Kaprowski et a., and that described by Kohler and Milstein, Nature 256:495 (1975), the disclosures of which are hereby incorporated by reference in their entirety. Typically, preparing monoclonal antibodies involves first immunizing a suitable target animal host with a selected immunogen comprising a polysaccharide or polysaccharide-protein conjugate of the present invention. The immunization is conducted in a manner sufficient to elicit B lymphocytes to produce or express antibodies that specifically bind to the polysaccharide. Alternatively, the lymphocytes are immunized in vitro.

The lymphocytes are then fused with an immortalized cell line using a suitable fusing agent, such as polyethylene glycol, to form a hybridoma cell. See Goding, Monoclonal Antibodies: Principles and Practice, Academic Press, (1986) pp. 59-103, the disclosure of which is hereby incorporated by reference in its entirety. The source of the lymphocytes determines whether the monoclonal antibodies are of human or animal origin. In general, peripheral blood lymphocytes ("PBLs") are used if antibodies and cells of human origin are desired, and spleen cells or lymph node cells are used if non-human mammalian sources are desired.

Immortalized cell lines are usually transformed mammalian cells, particularly myeloma cells of rodent, bovine and human origin. Usually, rat or mouse myeloma cell lines are employed. The hybridoma cells are cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Immortalized cell lines are chosen for practical considerations such as species of origin, fusion and growth characteristics. For example, suitable immortalized cell lines are those that fuse efficiently, support stable high level expression of antibody by the selected antibody-producing cells, and are sensitive to a medium such as HAT medium. Examples of immortalized cell lines include: murine myeloma lines, which can be obtained from the Salk Institute Cell Distribution Center, San Diego, Calif. and the American Type Culture Collection, Manassas, Va. Human myeloma and mouse-human heteromyeloma cell lines also have been described for the production of human monoclonal antibodies. See Kozbor, J. Immunol., 133:3001 (1984); and Brodeur et al., Monoclonal Antibody Production Techniques and Applications, Marcel Dekker, Inc., New York, (1987) pp. 51-63, the disclosures of which are hereby incorporated by reference in their entirety.

The monoclonal antibody is secreted into the culture medium by the hybridoma cells. The culture medium is then assayed for the presence of monoclonal antibodies that recognize and bind the polysaccharide. The anti-polysaccharide binding specificity of particular monoclonal antibodies produced by the hybridoma cells is determined by one of numerous procedures that are well known in the art. For example, antibody binding specificity may be determined by immunoprecipitation, radioimmunoassay (RIA), western blot, enzyme-linked immunoabsorbent assay (ELISA) or surface plasmon resonance (e.g. Biacore). See Harlow and Lane, "Antibodies: A Laboratory Manual," Cold Spring Harbor Laboratory, the disclosure of which is hereby incorporated by reference in its entirety. The precise epitope recognized by the monoclonal antibody is determined by epitope mapping. Such techniques and assays are well known in the art. The binding affinity of the monoclonal antibody can, for example, be determined by Scatchard analysis. See Munson et al., Anal. Biochem., 107:220 (1980).

After hybridoma cells producing antibodies with the desired specificity are identified, the clones are subcloned by limiting dilution and cultured using standard methods [Goding, supra]. Suitable culture media for this purpose include, for example, Dulbecco's Modified Eagle's Medium and RPMI-1640 medium. Alternatively, the hybridoma cells are grown in vivo as ascites in a mammal. The monoclonal antibodies secreted by the subclones are isolated or purified from the culture medium or ascites fluid by conventional immunoglobulin purification procedures such as, for example, protein A-Sepharose, hydroxylapatite chromatography, gel electrophoresis, dialysis, or affinity chromatography.

Alternatively, antibodies having the desired specificity and from the desired species of origin can be obtained through the use of phage display libraries. Additionally, examples of methods and reagents particularly amenable for use in generating and screening antibody display library can be found in, for example, U.S. Pat. No. 5,223,409; International Application WO 92/18619; International Application WO 91/17271; International Application WO 92/20791; International Application WO 92/15679; International Application WO 93/01288; International Application WO 92/01047; International Application WO 92/09690; International Application WO 90/02809; the disclosures of which are hereby incorporated by reference in their entirety.

Numerous references, including patents, patent applications and various publications are cited and discussed in the description of the multiple embodiments of the invention. The citation and/or discussion of such references is provided merely to clarify the description of the multiple embodiments of the invention and is not an admission that any such reference is "prior art" to the invention described herein. All references cited and/or discussed in this specification are incorporated herein by reference in their entirety and to the same extent as if each reference was individually incorporated by reference.

EXAMPLES

Particular embodiments of the present invention are described by way of the following examples. However, the use of these or other examples anywhere in the specification is illustrative only and in no way limits the scope and meaning of the invention or any exemplified term. Likewise, the invention is not limited to any embodiment described herein. Indeed, many modifications and variations of the invention may be apparent to those skilled in the art upon reading this specification and can be made without departing from its spirit and scope.

Example 1

Reduction of Unwanted Polysaccharide Levels in *H. Pylori*

This *H. pylori* phosphomannomutase (pgm) gene was disrupted to reduce the overall level of polysaccharides produced by *H. pylori* and to facilitate purification of high molecular weight external glycocalyx polysaccharides. To do this the *H. pylori* genomic sequence from The Institute for Genomic Research (TIGR) was obtained for the pgm gene.

A. PCR Amplification of *Helicobacter Pylori* Pgm Gene

Based on the DNA sequence of the suspected pgm open reading frame (orf), PCR primers corresponding to the start and stop of the gene were designed and synthesized. The forward primer had an NcoI site engineered at the start of the gene and the reverse primer had a BamHI site added at the end of the gene sequence.

FWD primer

5'-GGCGCCATGGACATTAGCATTTTTAGAGAATAC-3'

REV primer

5'-GGCGGATCCGAGATTATCCCAAGCTCTATTTTAAAG-3'

PCR amplification of the pgm gene was achieved for three strains using conditions of one minute denature at 94° C., one minute annealing at 50° C., and 80 sec extension at 72° C. for 30 cycles. *H. pylori* genomic DNA from strains PBCC 1103, PBCC 1105 and PBCC 1107 all produced a 1.4 kb product when they were used as templates in the PCR reaction, and were cloned into the PCR2.1 vector purchased from Invitrogen (Carlsbad, Calif.).

B. Construction of *H. Pylori* Pgm Deficient Strain (PBCC 1114)

A deletion in the cloned pgm gene (in pPX7763) was made by cleaving two internal Eco47111 sites. This enzyme cut the 1377 bp gene at positions 472 and 994, generating a 523 bp deletion into which the kanamycin gene from pUC4KAN was inserted (pPX7767). This plasmid was electroporated into ATCC 43504 and transformants selected on kanamycin (5 μg/ml). Two candidates were selected for further characterization. Silver stained SDS-PAGE gels of purified LPS confirmed that the transformants had a LPS of lower molecular weight than the parental strain. One of these isolates was confirmed for the mutation by Southern hybridization and given the strain designation PBCC 1114.

C. Growth of i H. Pylori Pgm Deficient Strain (PBCC 1114)

Cultures of *H. pylori* PBCC 1114 and were grown at 37° C. on Columbia broth agar plates with 10% defibrinated horse blood and 10 mg/ml vancomycin in a microaerophilic chamber. Liquid cultures of *H. pylori* strains were grown at 37° C. in BHI medium with 4% fetal calf serum and 10 mg/ml vancomycin in flasks infused with a gas mixture of 10% $CO_2$/6% $O_2$/84% $N_2$ (vol/vol/vol).

Example 2

Characterization of High Molecule Weight Polysaccharide from *H. Pylori*

A. Extraction of Extracellular Polysaccharides

The *H. pylori* strain PBCC 1114 described in example 1 was suspended in 300 ml of 0.04M $PO_4$/5 mM EDTA/0.02% $NaN_3$ buffer. Next, 600 mg of lysozyme (2 mg/ml) was added to the bacterial suspension. The reaction mixture was stirred at 4° C. for 2 days. The suspension was treated with 30 mg of RNAse, 30 mg of DNAse and incubated at 37° C. in a water bath for 4 hours. This reaction mixture was heated to 70° C. and extracted with hot (70° C.) phenol (300 ml) for 15 minutes. See O. Westphal & K. Jann, *Methods Carbohydr. Chem.* 5, 83-91 (1965), the disclosure of which is hereby incorporated by reference in its entirety.

The reaction mixture with the added phenol was cooled in an ice-water bath and then centrifuged at 5,000 rpm for 30 minutes. The aqueous supernatant was removed and the phenol layer was re-extracted with water (300 ml) at 70° C. for 15 minutes. The mixture was cooled and centrifuged at 5,000 rpm for 30 minutes. The aqueous supernatant was removed, pooled with the first aqueous extraction, and centrifuged at 8,000 RPM for 30 minutes to remove residual phenol. This supernatant, containing the water-soluble *H. pylori* polysaccharide, was collected and passed through a column of Bio-Gel P-6 (1 m×1 cm) with water as eluent at room temperature. The purified polysaccharide was collected in the high MW range and lyophilized.

B. Sugar Composition Analysis

Sugar composition analysis was performed by the alditol acetate method. See Sawardeker, et al., A. *Anal. Chem.* 37:1602-1604 (1965), the disclosure of which is hereby incorporated by reference in its entirety. The hydrolysis of 0.5 mg of sample was done in 4M-trifluoroacetic acid at 100° C. for 4 hours followed by evaporation under a nitrogen stream. Reduction in H$_2$O with NaBD$_4$ was accomplished overnight. Water was removed under nitrogen stream after addition of 0.3 ml of methanol. Subsequent acetylation with acetic anhydride and with residual sodium acetate as the catalyst was performed at 100° C. for 2 hours. The resultant solvent was removed by using a stream of nitrogen. The alditol acetate derivatives were extracted with chloroform. The monosaccharide alditol acetate derivatives were characterized by gas-liquid chromatography and mass spectrometry using a Hewlett-Packard chromatograph equipped with a 30-m DB-17 capillary column (210° C. (30 min)→240° C. at 2° C./min), and mass spectra were recorded using a Varian Saturn II mass spectrometer in the electron impact mode. Enantiomeric configurations of the monosaccharides, collected after hydrolysis of the capsule PS with 4M TFA for 4 hours at 100° C., were determined by the formation of the respective 2-(S)— and 2-(R)-butyl chiral glycosides. See K. Leontein et. al. *Carbohydr. Res.*, 62:359-362 (1978), the disclosure of which is hereby incorporated by reference in its entirety. The monosaccharide 2-(S)- and 2-(R)-butyl chiral glycoside derivatives were characterized by gas-liquid chromatography and mass spectrometry using a Hewlett-Packard chromatograph equipped with a 30-m DB-17 capillary column (210° C. (30 min)→240° C. at 2° C./min).

C. Sugar Linkage-site Analysis

The methylation linkage analysis was carried out by the NaOH/Me$_2$SO/CH$_3$I procedure. See I. Ciucanu, & F. Kerek, *Carbohydr. Res.* 131:209-217 (1984), the disclosure of which is hereby incorporated by reference in its entirety. The sample (1 mg) was methylated with methyl iodide (2 ml) in DMS (3 ml) with vigorous stirring in the presence of powdered sodium hydroxide (1 mg). The methylated derivative was extracted with chloroform. The methylated derivatives were hydrolyzed in 4M-trifluoroacetic acid at 100° C. for 4 hours followed by evaporation under a nitrogen stream. Reduction in H$_2$O with NaBD$_4$ was performed overnight. Water was removed under nitrogen stream after addition of 0.3 ml of methanol. Subsequent acetylation with acetic anhydride and with residual sodium acetate as the catalyst was accomplished at 100° C. for 2 hours. The resultant solvent was removed by a stream of nitrogen. The permethylated alditol acetate derivatives were extracted with chloroform. The monosaccharide alditol acetate derivatives were characterized by gas-liquid chromatography and mass spectrometry using a Hewlett-Packard chromatograph equipped with a 30-m DB-17 capillary column (DB-17 column, isothermally at 190° C. for 60 minutes), and mass spectra were recorded using a Varian Saturn II mass spectrometer in the electron impact mode.

Example 3

Chemical Composition and Structure of the Isolated Polysaccharide

Figure 1B:
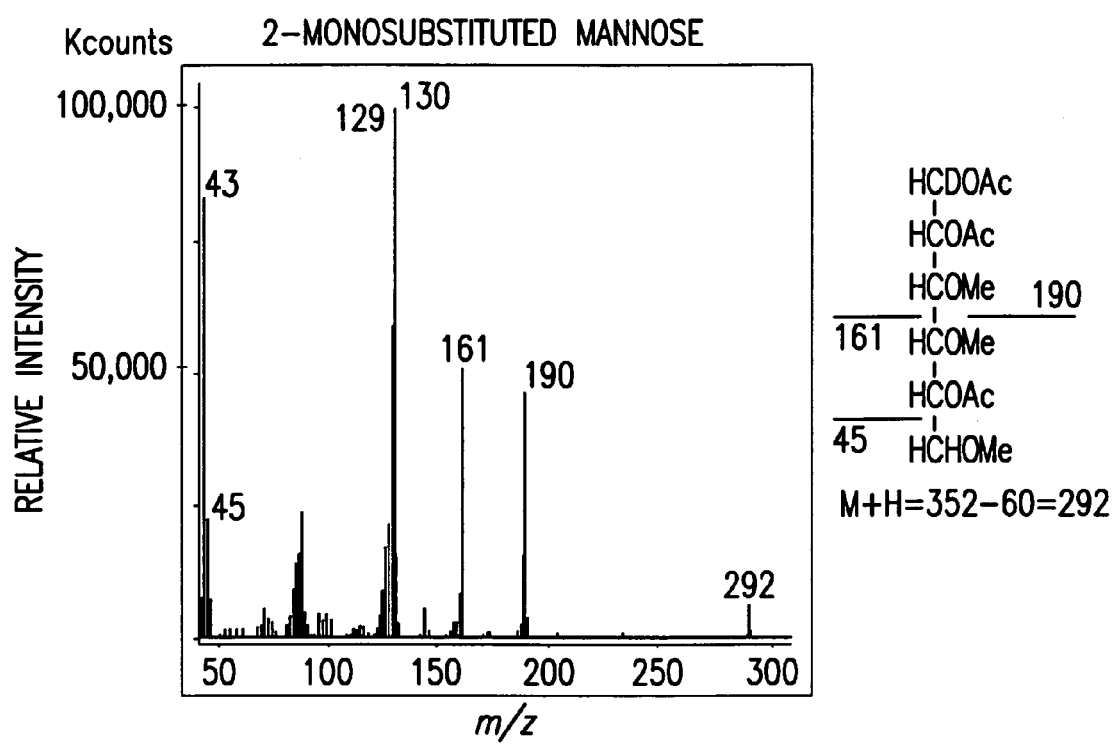
Figure 1C:
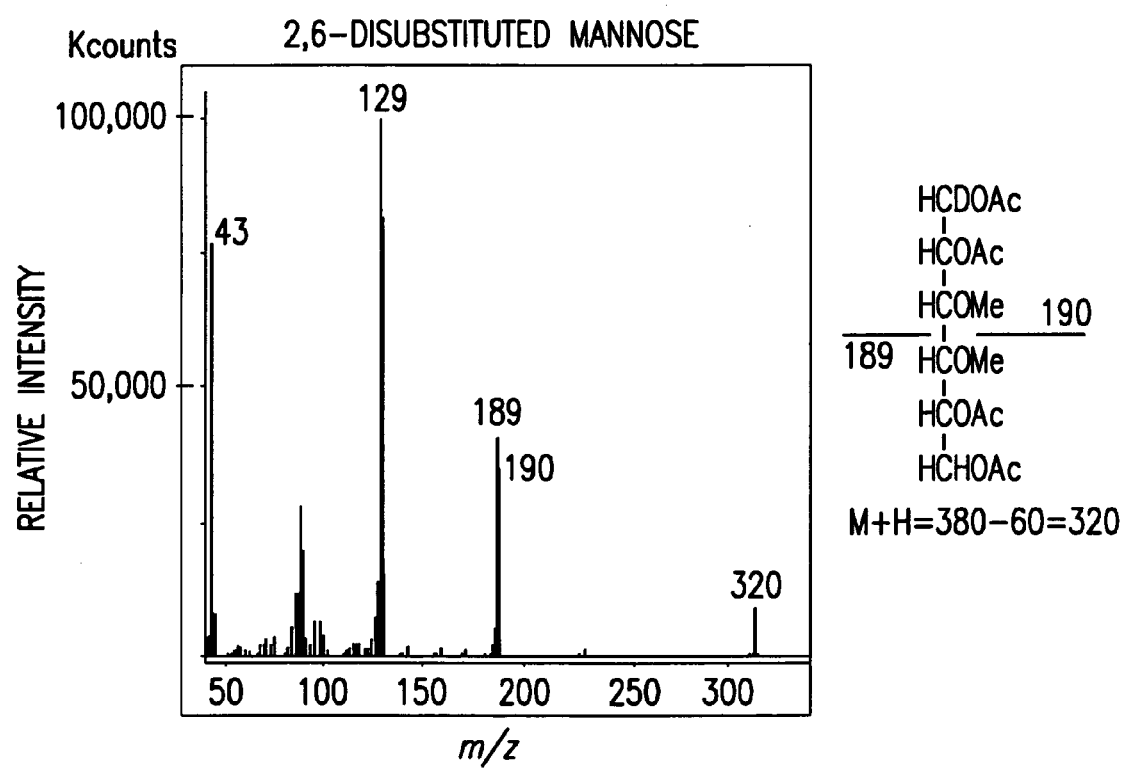

The structure of the polysaccharide isolated from the PBCC1114 mutant by the methods described above was investigated using chemical and spectroscopic methods. A sugar composition analysis by the alditol acetate and 2-(S, R)-butyl chiral glycoside methods revealed that this *H. pylori* polysaccharide was composed of D-mannose (Man) units. See Sawardeker, et. al., A. *Anal. Chem.* 37:1602-1604 (1965); K. Leontein et. al. *Carbohydr. Res.*, 62:359-362 (1978), the disclosure of which are hereby incorporated by reference in their entirety. A sugar linkage analysis by the methylation procedure showed that D-mannose was present as terminal unsubstituted (Man-1→) (FIG. 1A), 2-substituted (→2-Man-1→) (FIG. 1B), and 2,6-disubstituted (→2/6-Man-1→) (FIG. 1C) residues in quasi-equimolar ratios [see FIG. 1 for mass spectral (MS) fragmentation of the polysaccharide monosaccharide components from gas liquid chromatogram-mass spectrometer (GLC-MS)]. See I. Ciucanu, & F. Kerek, *Carbohydr. Res.* 131:209-217 (1984), the disclosure of which is hereby incorporated by reference in its entirety. This monosaccharide composition data indicates that the *H. pylori* polysaccharide is composed of a linear backbone of 1→2 linked mannose units in which approximately half are further substituted at the O-6 position (FIG. 2) and as shown below:

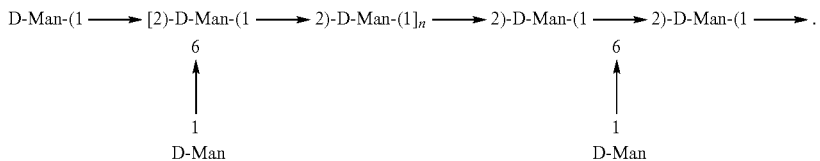

Example 4

Use of Purified Polysaccharide in a *H. Pylori* Immunogenic Composition

Sera pooled from 10 individuals (*H. pylori* infects 50% of the human population) reacted in a dot-blot analysis with the purified *H. pylori* polysaccharide which indicates that antibodies against this polysaccharide are produced and present in humans and can be used as a measure of past or current infection.

What is claimed is:

1. An isolated bacterial polysaccharide, comprising a repeating trisaccharide unit with a structure of

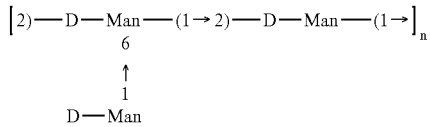

wherein n is an integer of between 3 and 100 and the polysaccharide is water soluble.

2. The polysaccharide of claim 1, wherein the repeating polysaccharide structure is a polysaccharide of *H. pylori*.

3. The polysaccharide of claim 1, wherein n is between about 10 and about 30.

4. The polysaccharide of claim 1, wherein the molecular weight of said polysaccharide is between about 5,000 Daltons and about 15,000 Daltons.

5. The polysaccharide of claim 1, wherein said polysaccharide is isolated and purified by a process comprising the steps of:
   a) extracting *H. pylori* bacteria with a mixture of water and phenol;
   b) size fractionating the water layer of step a) by column chromatography; and
   c) selecting those fractions containing said polysaccharide.

6. A branched polymannose polysaccharide, comprising a repeating trisaccharide unit, wherein the mannose residues are connected as shown below:

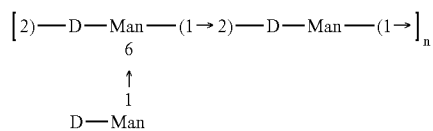

wherein n is an integer of between 3 and 100 and the polysaccharide is water soluble.

7. The branched polymannose polysaccharide of claim 6, wherein n is between about 10 and about 30.

8. The branched polymannose polysaccharide of claim 6, wherein the molecular weight of said polysaccharide is between about 5,000 Daltons and about 15,000 Daltons.

9. The branched polymannose polysaccharide of claim 6, wherein said polysaccharide is chemically synthesized.

10. An isolated bacterial polysaccharide, comprising a repeating trisaccharide unit,

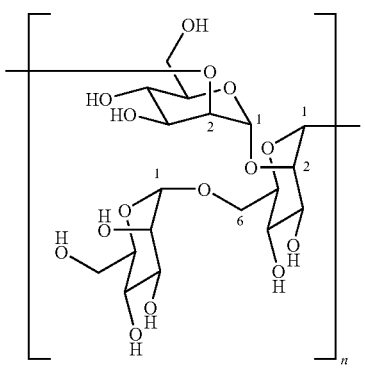

and wherein n is an integer of between 3 and 100 and the polysaccharide is water soluble.

11. The polysaccharide of claim 10, wherein the repeating polysaccharide structure is a polysaccharide of *H. pylori*.

12. The polysaccharide of claim 10, wherein n is between about 10 and about 30.

13. The polysaccharide of claim 10, wherein the molecular weight of said polysaccharide is between about 5000 Daltons and about 15,000 Daltons.

14. The polysaccharide of claim 11, wherein said polysaccharide is isolated and purified by a process comprising the steps of:
   a) extracting *H. pylori* bacteria with a mixture of water and phenol;
   b) size fractionating the water layer of step a) by column chromatography; and
   c) selecting those fractions containing said polysaccharide.

15. An immunogenic composition comprising an immunogenic amount of a polysaccharide and a pharmaceutically acceptable diluent, and wherein said polysaccharide comprises a repeating trisaccharide unit with a structure of

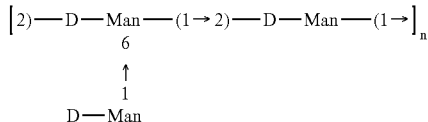

wherein n is an integer of between 3 and 100 and the polysaccharide is water soluble.

16. The immunogenic composition of claim 15, wherein the repeating polysaccharide structure is a polysaccharide of *Helicobacter pylori*.

17. The immunogenic composition of claim 15, further comprising an adjuvant.

18. The immunogenic composition of claim 15, wherein n is between about 10 and about 30.

19. The immunogenic composition of claim 15, wherein the molecular weight of said polysaccharide is between about 5,000 Daltons and about 15,000 Daltons.

20. The immunogenic composition of claim 15, comprising a polysaccharide wherein said polysaccharide is isolated and purified by a process comprising the steps of:
   a) extracting *H. pylori* bacteria with a mixture of water and phenol;
   b) size fractionating the water layer of step a) by column chromatography; and
   c) selecting those fractions containing said polysaccharide.

21. The immunogenic composition of claim 15, wherein said polysaccharide has been chemically synthesized.

22. An immunogenic composition comprising an immunogenic amount of a polysaccharide-protein conjugate and a pharmaceutically acceptable diluent, and wherein said polysaccharide comprises the repeating trisaccharide unit of claim 1, and wherein said polysaccharide and said protein are connected through covalent bonds.

23. The immunogenic composition of claim 22, wherein said protein is a protein selected from the group consisting of hemolysin, tetanus toxoid, cholera toxin, diphtheria toxoid and $CRM_{197}$.

24. The immunogenic composition of claim 22, wherein said polysaccharide and said protein are conjugated together directly through a covalent bond.

25. The immunogenic composition of claim 22, wherein said polysaccharide and said protein are conjugated together through a linker.

26. The immunogenic composition of claim 22, wherein said immunogenic composition further comprises an adjuvant.

27. The immunogenic composition of claim 22, wherein n is between about 10 and about 30.

28. The immunogenic composition of claim 22, wherein the molecular weight of said polysaccharide is between about 5,000 Daltons and about 15,000 Daltons.

29. The immunogenic composition of claim 22, wherein n is between about 30 and about 90.

30. The immunogenic composition of claim 22, wherein said polysaccharide is isolated from *H. pylori*.

31. The immunogenic composition of claim 30, comprising a polysaccharide wherein said polysaccharide is isolated and purified by a process comprising the steps of:
   a) extracting *H. pylori* bacteria with a mixture of water and phenol;
   b) size fractionating the water layer of step a) by column chromatography; and
   c) selecting those fractions containing said polysaccharide.

32. The immunogenic composition of claim 22, wherein said polysaccharide has been chemically synthesized.

33. A polysaceharide-protein conjugate comprising an immunogenic amount of an extracellular polysaccharide covalently linked to a protein, wherein said polysaccharide comprises the repeating trisaccharide unit of claim 1.

34. The polysaccharide-protein conjugate of claim 33, wherein said polysaccharide has a value of n that is between about 10 and about 30.

35. The polysaccharide-protein conjugate of claim 33, wherein said polysaccharide has a molecular weight of between about 5,000 Daltons and about 15,000 Daltons.

36. The polysaccharide-protein conjugate of claim 33, wherein said polysaccharide is isolated and purified from *H. pylori*.

37. The polysaccharide-protein conjugate of claim 33, wherein said polysaccharide is prepared synthetically.

38. The polysaccharide-protein conjugate of claim 33, wherein said protein is selected from the group consisting of hemolysin, tetanus toxoid, cholera toxin, diphtheria toxoid and $CRM_{197}$.

39. The polysaccharide-protein conjugate of claim 38, wherein there are between about 1 and about 20 molecules of conjugated polysaccharide per protein molecule.

40. The polysaccharide-protein conjugate of claim 33, further comprising a pharmaceutically acceptable diluent.

41. The polysaccharide-protein conjugate of claim 33, further comprising an adjuvant.

42. A method of immunizing a mammal against *H. pylori* infection comprising administering to an individual an immunogenic amount of the polysaccharide of claim 1.

43. The method of claim 42, wherein said repeating trisaccharide is a polysaccharide of *Helicobacter pylori*.

44. The method of claim 42, wherein said polysaccharide has a value for n that is between about 10 and about 30.

45. The method of claim 42, wherein said polysaccharide has a molecular weight of between about 5,000 Daltons and about 15,000 Daltons.

46. The method of claim 42, wherein said immunogenic polysaccharide is covalently conjugated to a protein.

47. The method of claim 46, wherein said protein is selected from the group consisting of hemolysin, tetanus toxoid, cholera toxin, diphtheria toxoid and $CRM_{197}$.

48. A method of immunizing a mammal against *H. pylori* infection comprising administering to an individual an immunogenic amount of a polysaccharide-protein conjugate, wherein said polysaccharide comprises the repeating trisaccharide unit of claim 1, and wherein said polysaccharide and said protein are connected through covalent bonds.

49. The method of claim 48, wherein said polysaccharide has a value of n that is between about 10 and about 30.

50. The method of claim 49, wherein said polysaccharide has a molecular weight of between about 5,000 Daltons and about 15,000 Daltons.

51. The method of claim 48, wherein said polysaccharide is isolated from *H. pylori*.

52. The method of claim 48, wherein said polysaccharide is prepared synthetically.

53. The method of claim 48, wherein said protein is selected from the group consisting of hemolysin, tetanus toxoid, cholera toxin, diphtheria toxoid and $CRM_{197}$.

54. The method of claim 53, wherein there are between about 1 and about 20 molecules of conjugated polysaccharide per protein molecule.

55. The method of claim 48, wherein said polysaccharide protein conjugate further comprises a pharmaceutically acceptable diluent.

56. The method of claim 48, wherein said polysaccharide protein conjugate further comprises an adjuvant.

* * * * *

SEQUENCE LISTING

<160> NUMBER OF SEQ ID NOS: 2

<210> SEQ ID NO 1
<211> LENGTH: 33
<212> TYPE: DNA
<213> ORGANISM: Artificial
<220> FEATURE:
<223> OTHER INFORMATION: Forward Primer for Amplification of
      Helicobacter Pylori pgm Gene

<400> SEQUENCE: 1
ggcgccatgg acattagcat ttttagagaa tac                                33

<210> SEQ ID NO 2
<211> LENGTH: 36
<212> TYPE: DNA
<213> ORGANISM: Artificial
<220> FEATURE:
<223> OTHER INFORMATION: Reverse Primer for PCR Amplification of
      Helicobacter Pylori pgm Gene

<400> SEQUENCE: 2
ggcggatccg agattatccc aagctctatt ttaaag                             36